(12) United States Patent  
Sankar

(10) Patent No.: US 8,581,778 B2  
(45) Date of Patent: Nov. 12, 2013

(54) PULSE COMPRESSION SYSTEM AND METHOD

(75) Inventor: Pat Sankar, Tustin, CA (US)

(73) Assignee: Scidea Research, Inc., Tustin, CA (US)

( * ) Notice: Subject to any disclaimer, the term of this patent is extended or adjusted under 35 U.S.C. 154(b) by 357 days.

(21) Appl. No.: 12/804,379

(22) Filed: Jul. 19, 2010

(65) Prior Publication Data

US 2012/0209113 A1   Aug. 16, 2012

(51) Int. Cl.
*G01S 13/32* (2006.01)
*G01S 15/32* (2006.01)
*A61B 8/00* (2006.01)

(52) U.S. Cl.
USPC ............ 342/201; 342/128; 367/101; 600/437

(58) Field of Classification Search
USPC ................. 342/128, 200, 201, 25 R–25 F
See application file for complete search history.

(56) References Cited

U.S. PATENT DOCUMENTS

| 2,939,017 | A |   | 5/1960  | Teasley et al. |
|-----------|---|---|---------|----------------|
| 4,318,019 | A |   | 3/1982  | Teasley et al. |
| 4,851,848 | A | * | 7/1989  | Wehner ........................ 342/25 D |
| 4,973,967 | A | * | 11/1990 | David et al. ................... 342/122 |
| 5,099,175 | A |   | 3/1992  | Schlueter et al. |
| 5,315,159 | A |   | 5/1994  | Gribnau |
| 5,387,918 | A | * | 2/1995  | Wiesbeck et al. ............. 342/128 |
| 5,541,944 | A |   | 7/1996  | Neil |
| 5,719,579 | A | * | 2/1998  | Torre et al. ..................... 342/13 |
| 5,808,580 | A | * | 9/1998  | Andrews, Jr. ................. 342/162 |
| 6,084,498 | A |   | 7/2000  | Stelter et al. |
| 6,188,147 | B1 |  | 2/2001  | Hazelton et al. |
| 6,356,177 | B1 |  | 3/2002  | Ogura et al. |
| 6,456,231 | B1 | * | 9/2002 | McEwan ......................... 342/93 |
| 7,042,109 | B2 |  | 5/2006  | Gabrys |
| 7,148,777 | B2 |  | 12/2006 | Chell et al. |
| 7,358,624 | B2 |  | 4/2008  | Bacon |
| 7,425,772 | B2 |  | 9/2008  | Novo Vidal |
| 7,715,166 | B2 |  | 5/2010  | Schultz et al. |

(Continued)

FOREIGN PATENT DOCUMENTS

JP        04201994       2/1994

OTHER PUBLICATIONS

Doerry, Armin W. "Generating Nonlinear FM Chrip Waveforms for Radar". Sandia National Laboratories. 34 pages. Sep. 2006.*
U.S. Appl. No. 13/607,595, Sankar, Pat.

(Continued)

*Primary Examiner* — Matthew M Barker
(74) *Attorney, Agent, or Firm* — Knobbe, Martens, Olson & Bear LLP

(57) ABSTRACT

A non-linear FM pulse compression system includes a non-linear FM transmitter adapted to receive an input signal and transmit an output signal. The non-linear FM transmitter is adapted to modulate the frequency of the output signal by at least one of the following: increasing the frequency of the output signal as a logarithmic function of the frequency of samples in the input signal; modulating the frequency of the output signal in inversely proportional relationship to the frequency of samples in the input signal; and modulating the frequency of the output signal according to a random permutation of the frequency of the input signal. At least one antenna interfaces with the non-linear FM transmitter. A non-linear FM receiver interfacing with the at least one antenna. The non-linear FM receiver is adapted to auto-correlate the output signal with a return signal.

11 Claims, 25 Drawing Sheets

(56) References Cited

U.S. PATENT DOCUMENTS

| | | | |
|---|---|---|---|
| 7,791,530 B2 * | 9/2010 | Puglia | 342/128 |
| 8,009,001 B1 | 8/2011 | Cleveland | |
| 8,035,551 B1 * | 10/2011 | Govoni | 342/189 |
| 8,264,314 B2 | 9/2012 | Sankar | |
| 2008/0074223 A1 | 3/2008 | Pribonic | |
| 2008/0084071 A1 | 4/2008 | Zhu | |
| 2008/0231052 A1 | 9/2008 | Farmer | |
| 2008/0315709 A1 | 12/2008 | Uchiyama | |
| 2010/0133853 A1 | 6/2010 | Masi et al. | |
| 2011/0031760 A1 | 2/2011 | Lugg | |
| 2011/0241349 A1 | 10/2011 | Sankar | |

OTHER PUBLICATIONS

U.S. Appl. No. 13/657,644, Sankar, Pat.
U.S. Appl. No. 13/657,736, Sankar, Pat.
U.S. Appl. No. 13/674,869, Sankar.

* cited by examiner

Non Linear versus Linear FM Modulation

Close Up View Detected Targets -0 dB noise

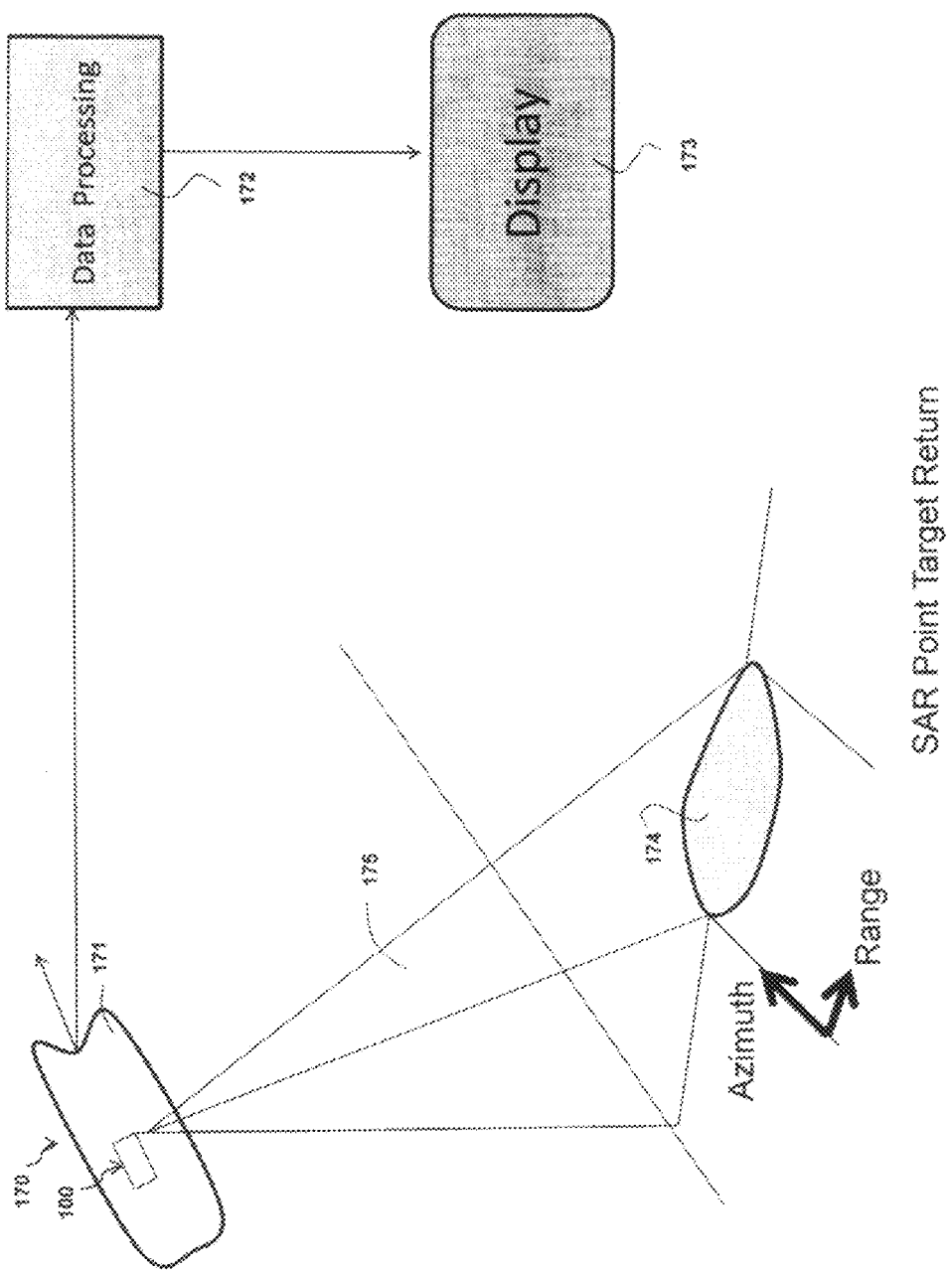

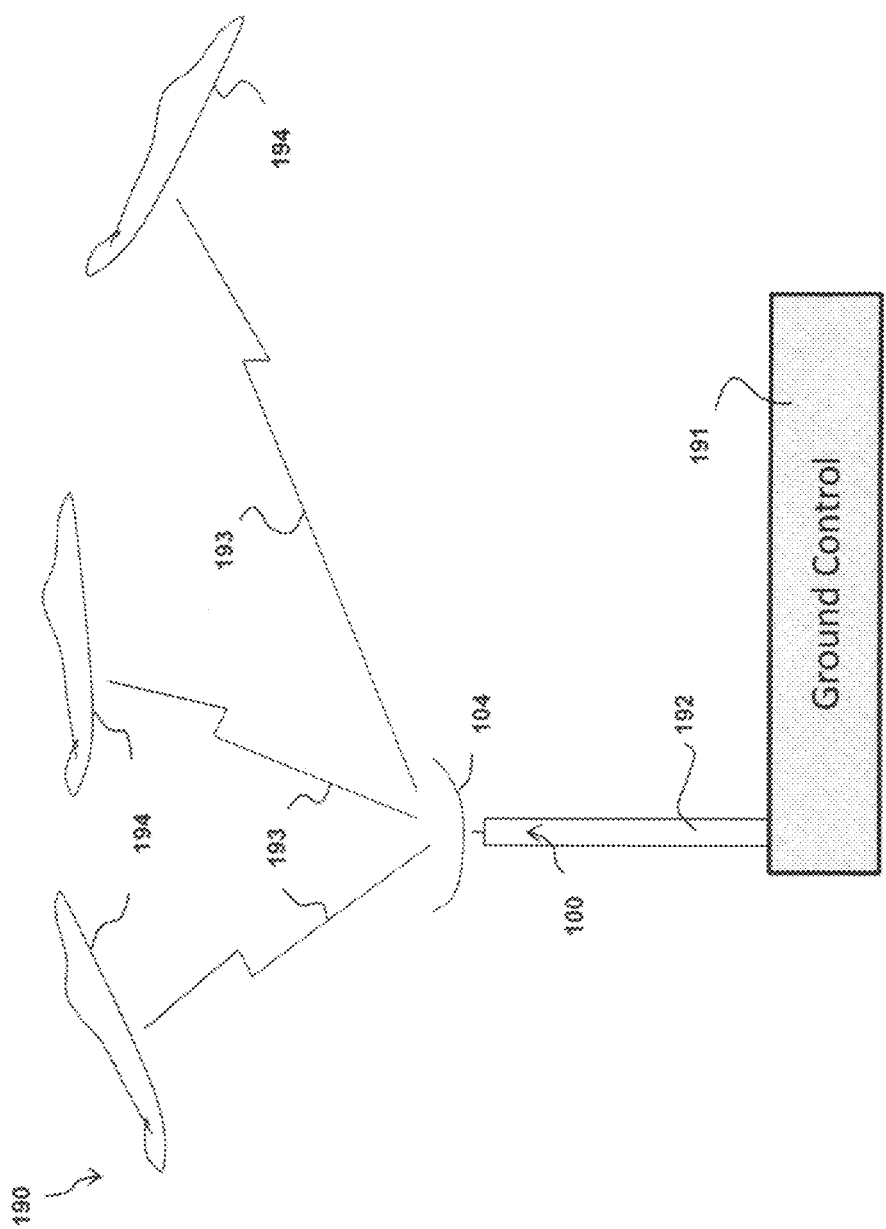

Free Electron LASER Embodiment 3

PULSE COMPRESSION SYSTEM AND METHOD

FIELD

The disclosure relates to high resolution RADAR, LIDAR and other applications. More particularly, the disclosure relates to a non-linear FM pulse compression system and method which enhances target resolution in RADAR, LIDAR and other applications.

BACKGROUND

The word RADAR is an acronym derived from the phrase RAdio Detection And Ranging and applies to electronic equipment designed for detecting and tracking objects (targets) at considerable distances. The basic principle behind radar is simple—extremely short bursts of radio energy (traveling at the speed of light) are transmitted, reflected off a target and then returned as an echo. The RADAR system correlates the return signal (appropriately corrected for gain) with the transmitted pulse to indicate the location of the target within a two or three dimensional framework. Among the various radar processing techniques, pulse compression is a signal processing technique mainly used not only in radar but also in sonar and echography to enhance the range resolution as well as the signal-to-noise ratio.

The rectangular pulse of an electromagnetic signal is given by [1]

$$P_r(t) = A\exp(-j2\pi f_c t) T/2 \leq t < T \quad (1)$$

where $f_c$ is the carrier frequency.

The linear FM chirp of an RF signal is given by $$P_{FM}(t) = A\exp(-j2\pi f_c t^2) T/2 \leq t < T \quad (2)$$

Various techniques for pulse compression of electromagnetic signals using variants of frequency modulation are known in the art. These include an AM-FM laser for improved accuracy of target range measurements and a LASER RADAR system which uses an optically linear modulated FM chirp signal. Another method proposes a random FM scheme for mobile radios including a non-linear FM modulation which is carried out by driving an FM modulator with random or chaotic sequences and deriving theoretical expressions for the spectral properties of the FM waveforms.

The conventional FM chirp techniques mentioned above either use linear FM modulation or propose the use of random input sequences to create non-linear FM signals with the perfect auto correlation function properties. However, these techniques are either too complicated to implement in many applications or do not result in optimal pulse compression. Moreover, conventional pulse compression techniques may not result in a range resolution which is optimal for the application. Therefore, a non-linear FM pulse compression system and method which can result an order of magnitude improvement in pulse compression and hence dramatically improve the resolution as well as the precision of range of detected targets in RADAR, LADAR and other applications is needed.

SUMMARY

The disclosure is generally directed to a non-linear FM pulse compression system. An illustrative embodiment of the system includes a non-linear FM transmitter adapted to receive an input signal and transmit an output signal. The non-linear FM transmitter is adapted to modulate the frequency of the output signal by at least one of the following: increasing the frequency of the output signal as a logarithmic function of the frequency of samples in the input signal; modulating the frequency of the output signal in inversely proportional relationship to the frequency of samples in the input signal; and modulating the frequency of the output signal according to a random permutation of the frequency of the input signal. At least one antenna interfaces with the non-linear FM transmitter. A non-linear FM receiver interfacing with the at least one antenna. The non-linear FM receiver is adapted to auto-correlate the output signal with a return signal.

The disclosure is further generally directed to a non-linear FM pulse compression method. An illustrative embodiment of the method includes providing an input signal; forming an output signal by modulating the frequency of the input signal by at least one of the following: increasing the frequency of the output signal as a logarithmic function of the frequency of samples in the input signal; modulating the frequency of the output signal in inversely proportional relationship to the frequency of samples in the input signal; and modulating the frequency of the output signal according to a random permutation of the frequency of the input signal; transmitting the output signal against a target; receiving a return signal from the target; and auto-correlating the output signal with the return signal.

The disclosure is further generally directed to a free electron laser system. An illustrative embodiment of the free electron laser system includes an undulator having a pair of spaced-apart parallel series of magnets having alternating poles; a laser cavity defined between the spaced-apart parallel series of magnets; and an electron source adapted to emit an electron beam through the laser cavity.

BRIEF DESCRIPTION OF THE DRAWINGS

The disclosure will now be made, by way of example, with reference to the accompanying drawings, in which:

FIG. 17 is a schematic diagram which illustrates implementation of an illustrative embodiment of the non-linear FM pulse compression system in a high resolution synthetic aperture application;

FIG. 19 is a schematic diagram which illustrates implementation of an illustrative embodiment of the non-linear FM pulse compression system in a high resolution air traffic control system application;

DETAILED DESCRIPTION

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the appended claims. Furthermore, there is no intention to be bound by any expressed or implied theory presented in the preceding technical field, background, brief summary or the following detailed description.

The disclosure is generally directed to a non-linear FM pulse compression system and method. Some embodiments may include non-linear mapping of the time sequence which results in a randomly frequency modulated signal. Some embodiments may accomplish the same result by random permutation of the carrier pulse signal.

In some embodiments, the frequency of the output non-linear FM chirp signal increases as a logarithmic function of the frequency of the samples in the input signal and is given by:

$$P_{LogFM}(t) = A\exp(-j2\pi f_c \log_2(t)) T/2 \leq t < T/2 \quad (3)$$

In some embodiments, the frequency changes in the non-linear FM chirp signal are inversely proportional to the frequency of the samples in the input pulse signal and are given by:

$$P_{InvFM}(t) = A\exp(-j2\pi f_c/t) T/2 \leq t < T/2 \quad (4)$$

In some embodiments, the frequency changes of the non-linear FM chirp signal are produced by a random permutation of the input pulse signal to create a random sinusoid:

$$P_{RandomFM}(t) = \text{Random Permutation}\{A\exp(-j2\pi f_c/t)\} T/2 \leq t < T/2 \quad (5a)$$

In some embodiments, the random permutation may be performed on the input to the sinusoid rather than the output:

$$P_{RandomFM}(t) = A\exp(\text{Random Permutation}\{-j2\pi f_c/t\}) T/2 \leq t < T/2 \quad (5b)$$

For some applications, however, performing the random permutation on the output of the sinusoidal pulse may be simpler.

Figure 1:
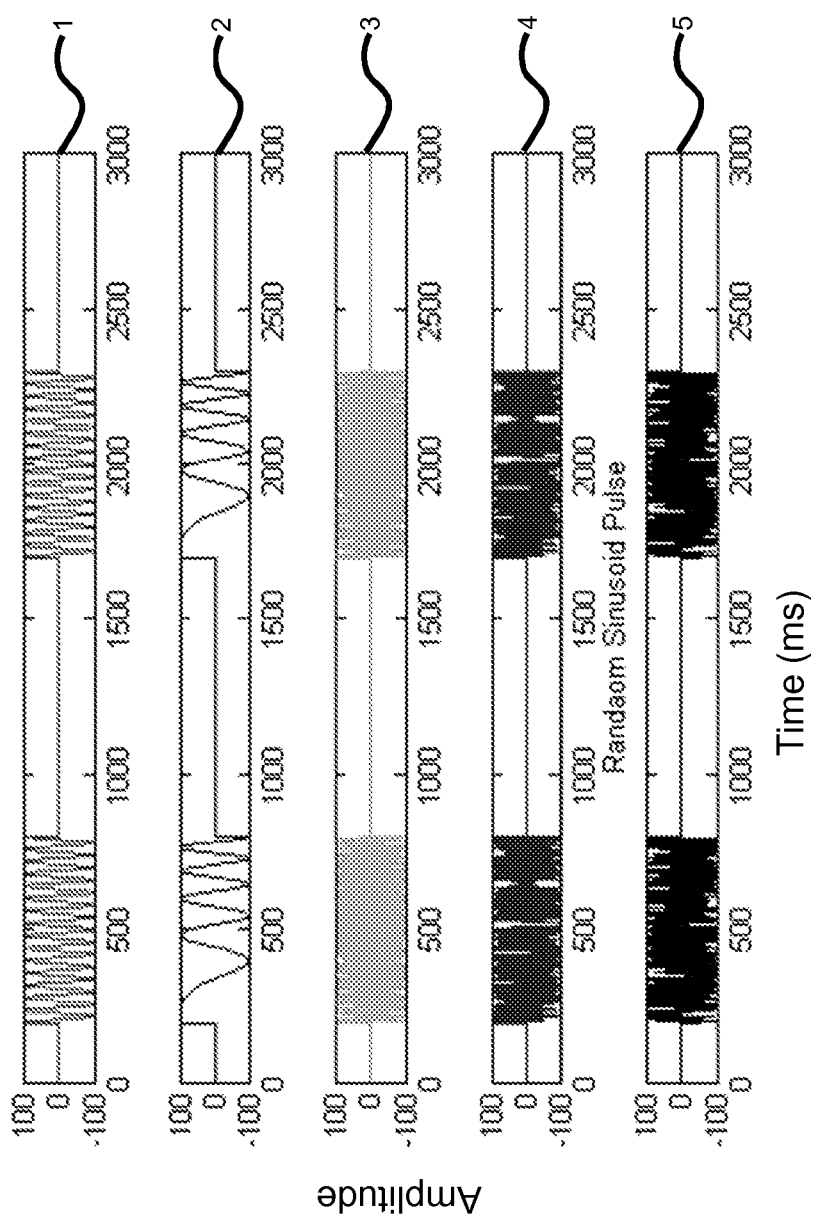
FIG. 1 is a graph which illustrates various types of pulse waveforms.
Figure 3:
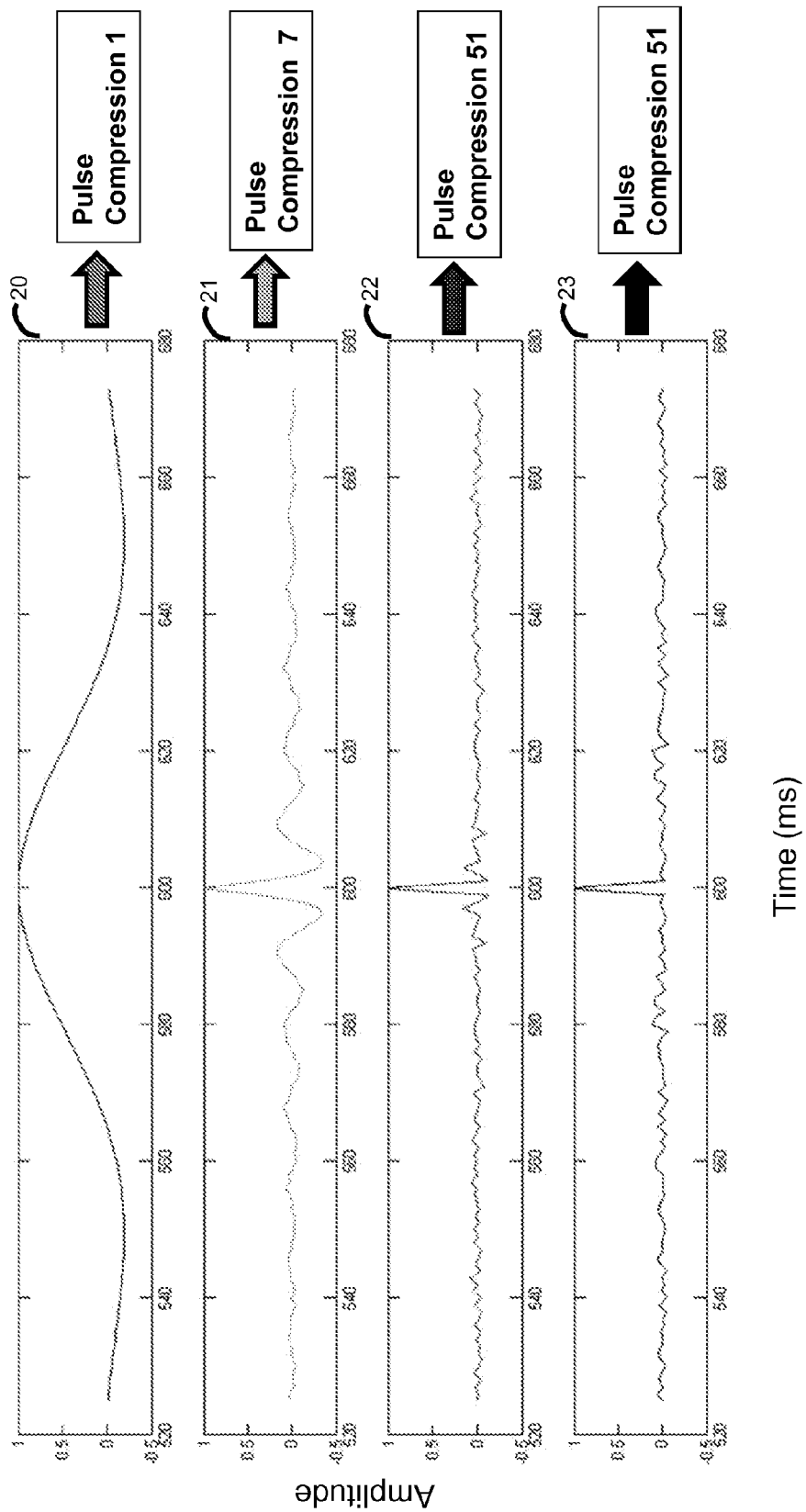
FIG. 3 is a graph which illustrates autocorrelation functions of the pulse waveforms illustrated in FIG. 1 with pulse compression factors.

Referring initially to FIG. 1 of the drawings, graph which illustrates various types of pulse waveforms is illustrated. The graph includes a square pulse waveform 1, a linear FM pulse waveform 2, a non-linear log FM pulse waveform 3, a non-linear inverse pulse waveform 4 and a non-linear random sinusoid FM pulse waveform 5. The non-linear log FM pulse waveform 3, the non-linear inverse pulse waveform 4 and the non-linear random sinusoid FM pulse waveform 5 have a near-random appearance, which is the fundamental reason why the auto correlation functions of the signals 21-23 which correspond to these waveforms almost resemble a delta function as shown in FIG. 3 whereas the auto correlation function of the signal which corresponds to the linear waveform 20 does not.

Figure 2:
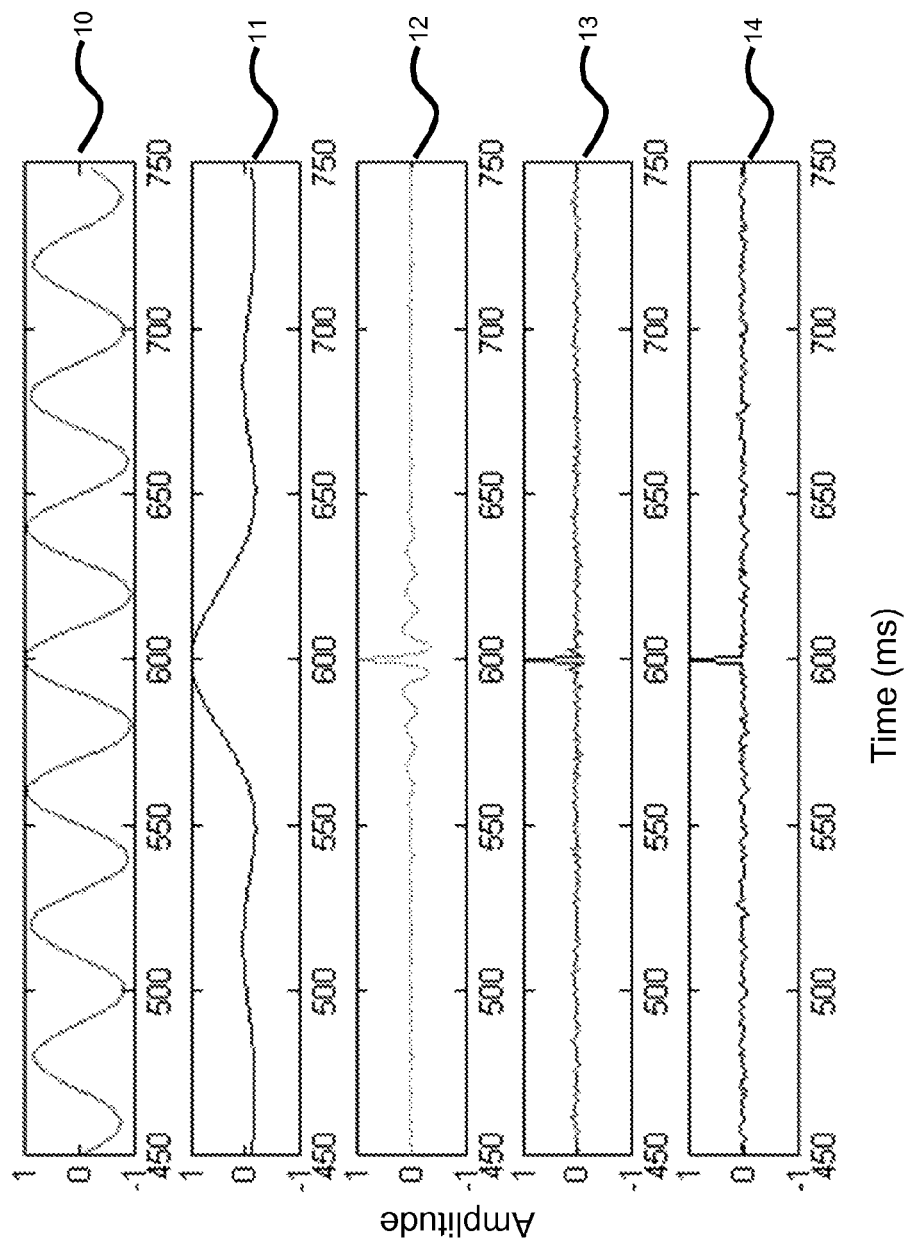
FIG. 2 is a graph which illustrates autocorrelation functions of the pulse waveforms illustrated in FIG. 1.

Referring next to FIG. 2 of the drawings, a graph which illustrates autocorrelation functions of the pulse waveforms illustrated in FIG. 1 is illustrated. Reference numerals 10-14 illustrate autocorrelation functions of the square pulse waveform 1, the linear FM pulse waveform 2, the non-linear log FM pulse waveform 3, the non-linear inverse FM pulse 4 and the non-linear random sinusoidal FM pulse 5, respectively, in FIG. 1. When the auto correlation functions 11-14 in FIG. 2 are compared, it is apparent that the auto correlation signal corresponding to the inverse FM chirp pulse 13 and the random sinusoidal chirp pulse 14 most resemble the delta function, a desired property for the optimally-compressed pulse. FIG. 3 illustrates the auto correlation functions of the various non-linear chirp signals 20-23, respectively, with the corresponding pulse compression factors.

Figure 5:
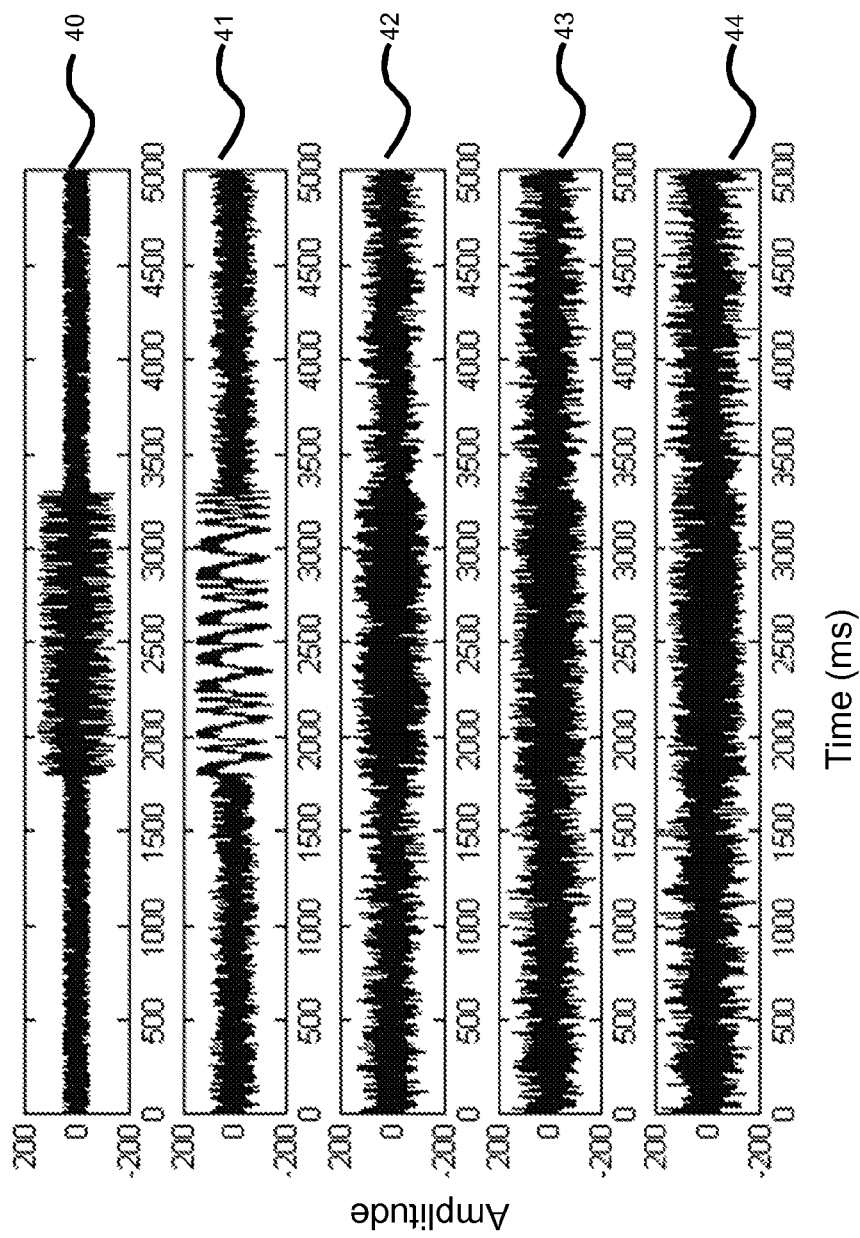
FIG. 5 is a graph which illustrates automatic gain control (AGC) corrected return echo signals for the pulse waveforms illustrated in FIG. 1.
Figure 6:
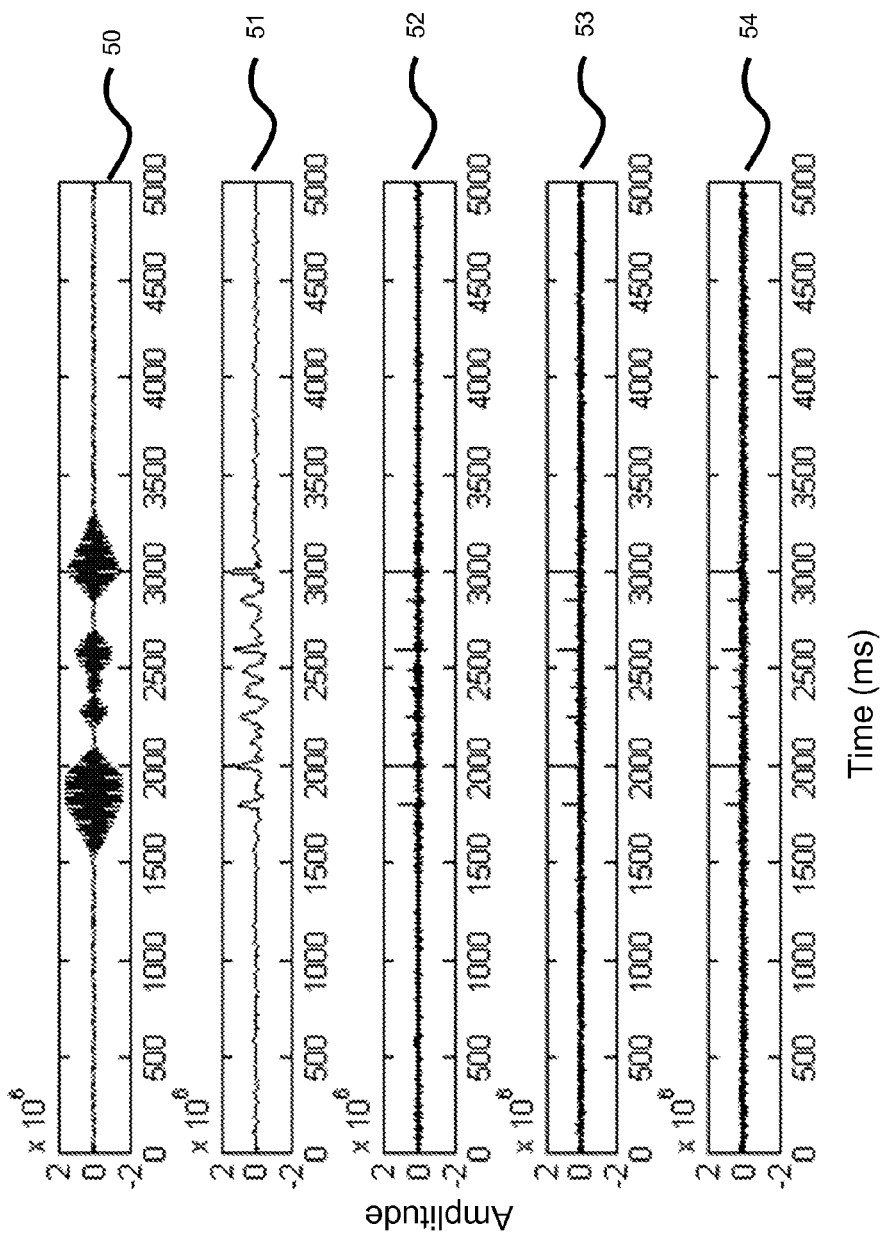
FIG. 6 is a graph which illustrates matched filter outputs for the pulse waveforms illustrated in FIG. 1.

It is possible to infer from FIG. 5 that the auto correlation function of the non-linear log FM pulse 42 and the non-linear inverse FM pulse 43 are compressed versions of the auto correlation functions of the linear square pulse 40 and linear FM pulse 41. If the compression ratio between the two sin c functions is $4*T/f_c$ where T is the pulse width in terms of the number of samples in the pulse, and $f_c$ is the base frequency of the FM modulation of the pulse, the plot of the theoretical and computed compression factors versus the various values of $f_c$ are shown in FIG. 6 and also in Table I.

TABLE I

| Carrier Frequency | Theoretical Pulse Compression Factor | Pulse Compression Factor Log FM | Pulse Compression Factor Inverse FM | Pulse Compression Factor Random FM |
|---|---|---|---|---|
| 25 | 96 | 15.86 | 55.5 | 111 |
| 50 | 48 | 14.57 | 51 | 51 |
| 100 | 24 | 12.5 | 25 | 25 |
| 200 | 12 | 4 | 8 | 8 |
| 400 | 6 | 3 | 6 | 6 |
| 800 | 3 | 3 | 3 | 3 |

The analytical expression for the auto correlation of the linear FM modulated signal 41 (FIG. 5) is given by the following equation [5]:

$$<s_{c'}, s_{c'}>(t) = T\Lambda\left(\frac{t}{T}\right) sinc\left[\pi\Delta ft\Lambda\left(\frac{t}{T}\right)\right]e^{2i\pi f_0 t} \quad (5)$$

Where T is the width of the pulse, and $\Lambda(t/T)$ is the triangle weighting function.

The maximum of the autocorrelation function of $s_{c'}$ is reached at 0. Around 0, this function behaves as the sin c term. The −3 dB temporal width of that cardinal sine is more or less equal to $$T' = \frac{1}{\Delta f}.$$

Everything happens as if, after matched filtering, the resolution that would have been reached with a simple pulse of duration T' is obtained. For the common values of $\Delta f$, T' is smaller than T, hence the pulse compression name.

Figure 4:
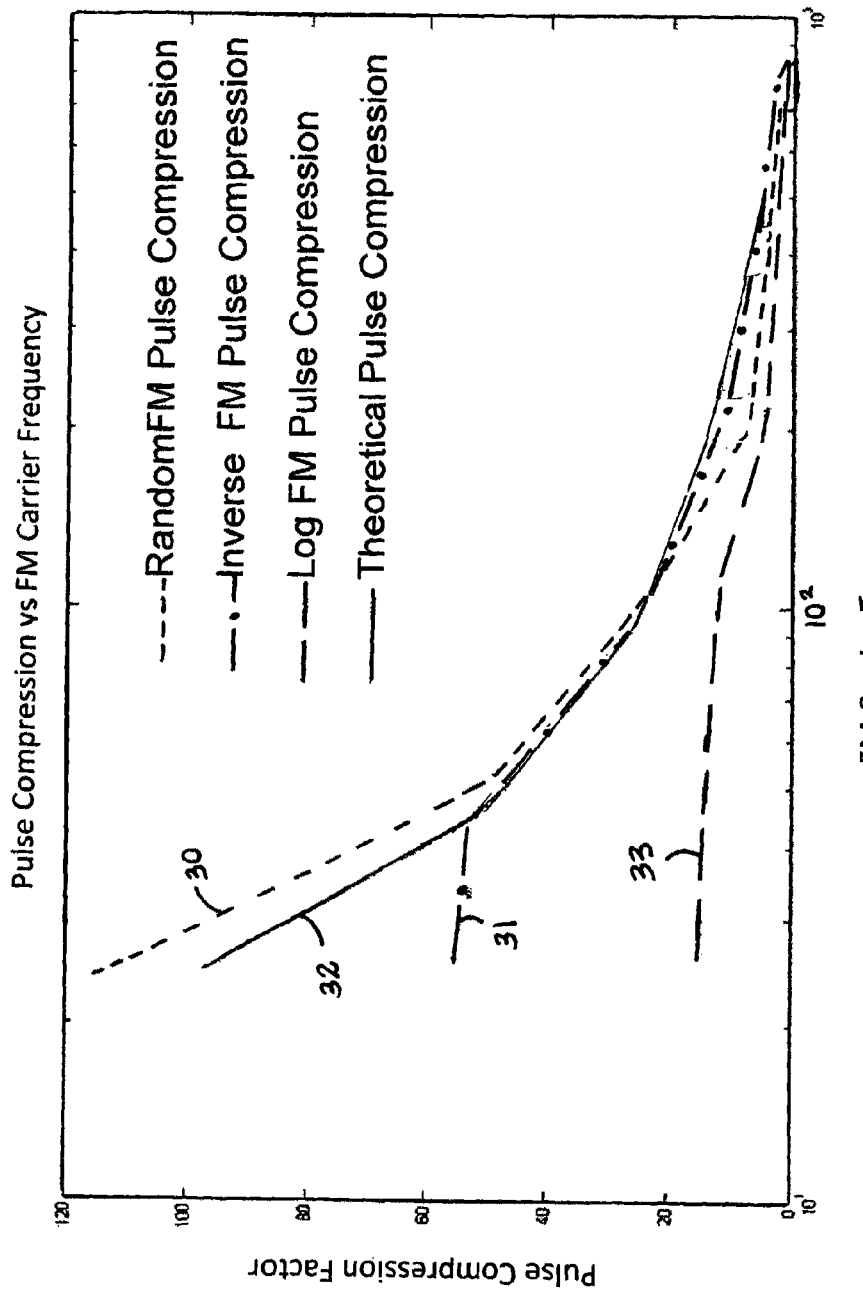
FIG. 4 is a line graph which illustrates theoretical estimates and computed pulse compression factors (y-axis) for non-linear FM signals for various values of the carrier frequency (x-axis)

Even though it cannot be rigorously proven, based on the comparisons of FIG. 3 and the non-linear vs. linear FM modulation of the random FM pulse compression the inverse FM pulse compression 31, the log FM pulse compression 32 and the theoretical pulse compression 33, as illustrated in FIG. 4, the autocorrelation function of the non-linear FM modulated signal is very similar to that of the linear FM modulated signal but with width of the main lobe further compressed as shown below:

$$T_{nfm} = T_{fm}/(M/f_c) \quad (6)$$

where M is the number of samples in the pulse and $f_c$ is the base frequency of the linear FM modulator and $T_{fm} = T'$.

Since energy is conserved for all three types of pulse waveforms $$P_r T_r = P_{fm} T_{fm} = P_{nfm} T_{nfm} \quad (7)$$

Where $P_r$, $T_r$, $P_{fm}$, $T_{fm}$, $P_{nfm}$ and $T_{nfm}$ are the power required and the main lobe half width of the rectangular pulse, linear FM modulated pulse and the nonlinear modulated FM pulse. Hence, the power required to transmit the non-linear FM modulated signal is given by $$P_{nfm} = P_{fm}(T_{fm}/T_{nfm}) = P_r(T_r/T_{nfm}) \quad (8)$$

The Radar range equation states that if $\tau$ is the time of travel of the pulse echo from the target, then the range r from the target is given by:

$$R = (c\tau)/2 \quad (9)$$

where c is the speed of light given by $3 \times 10^8$ m/s.

As an example, a radar experiment may include four targets closely separated by distances 270, 300, 337.5, 360, 373.5, 390.0, 427.5 and 450 meters respectively. Assuming a sampling rate of 1 Giga Hertz, the echolocations of these targets will be approximately 1800, 2000, 2250, 2400, 2490, 2600, 2850 and 3000 respectively.

In FIG. 5, the automatic gain control of corrected return signals in the presence of 0 dB background noise for all five types of pulse waveforms 40-44, respectively, is illustrated. The targets are buried in the return echo RF signal.

In FIG. 6, the automatic gain matched filter output in the presence of 0 dB background noise for all the five types of pulse waveforms 50-54, respectively, is illustrated. A careful examination clearly demonstrates the advantages of the linear FM signal 51 over the rectangular pulse 50 and the higher resolution provided by the non-linear FM modulated signals 52, 53, 54 over the linear FM signal.

Figure 7:
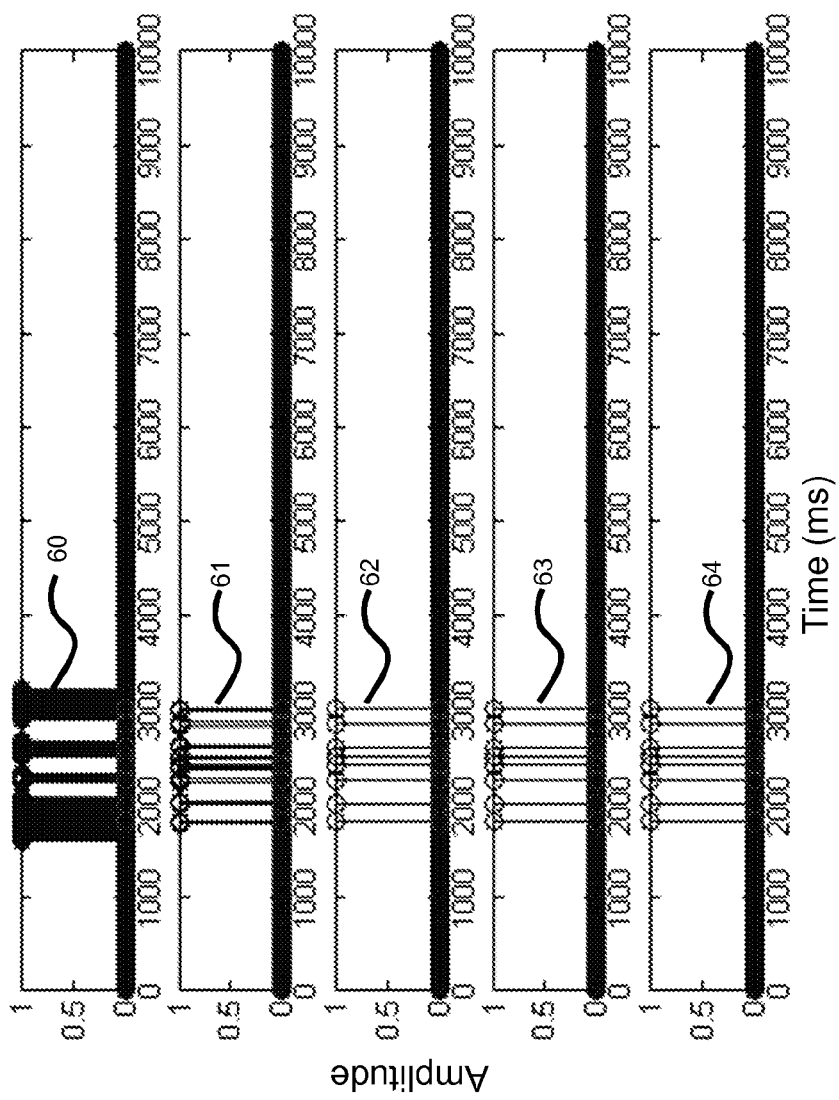
FIG. 7 is a graph which illustrates detected targets for the pulse waveforms illustrated in FIG. 1.
Figure 8:
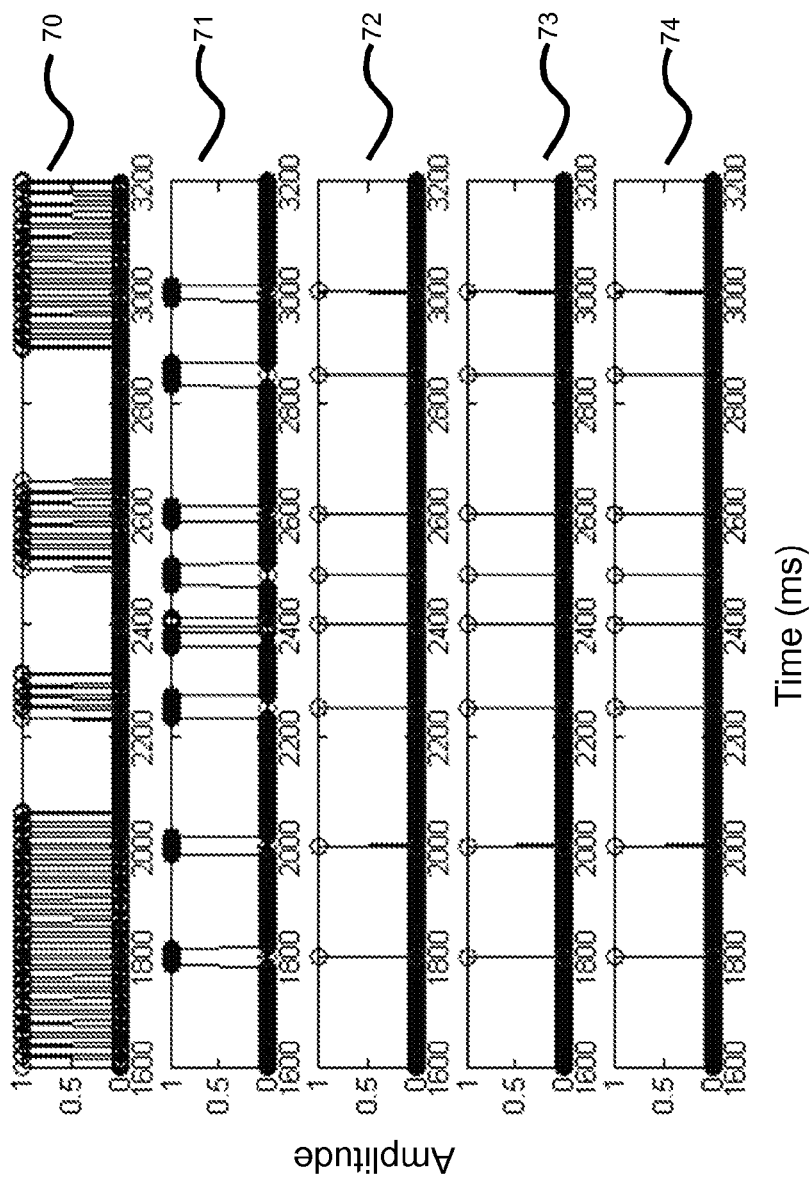
FIG. 8 is a close-up view of the detected targets for the pulse waveforms illustrated in FIG. 1.

In FIG. 7, the detected targets for each of the five signals 60-64, respectively, and a close-up of the same 70-74, respectively, are illustrated in FIG. 8. It is more clear from FIGS. 7 and 8 that the non-linear FM pulses (62-64, respectively, in FIGS. 7 and 72-74, respectively, in FIG. 8) provide the highest resolution in addition to improved accuracy for the targets over the rectangular pulse 60, 70 and the linear FM pulse 61, 71.

If a continuous pulse waveform is transmitted at a base frequency of $f_c$ and the measured frequency of the received pulse is $f_r$, then the Doppler shift $f_d$ in frequency is defined by $$f_t = f_c + f_d \text{ for approaching targets} \quad (10)$$

$$f_t = f_c - f_d \text{ for receding targets} \quad (11)$$

Radar Doppler shift frequency is a function of radar transmit frequency ($f_o$), speed of wave (c=speed of light), and target velocity ($v_t$). Note, $v_t$ is positive (+) for approaching targets and negative (−) for receding targets:

$$f_d = \pm 2v_t f_o/c \quad (12)$$

$$v_t = \pm cf_d/2f_o \quad (13)$$

It is also possible to use a CW radar system to measure range instead of range rate by frequency modulation, the systematic variation of the transmitted frequency. What this does in effect is to put a unique "time stamp" on the transmitted wave at every instant. By measuring the frequency of the return signal, the time delay between transmission and reception can be measured and therefore the range determined as before. Of course, the amount of frequency modulation must be significantly greater than the expected Doppler shift or the results will be affected.

Figure 9:
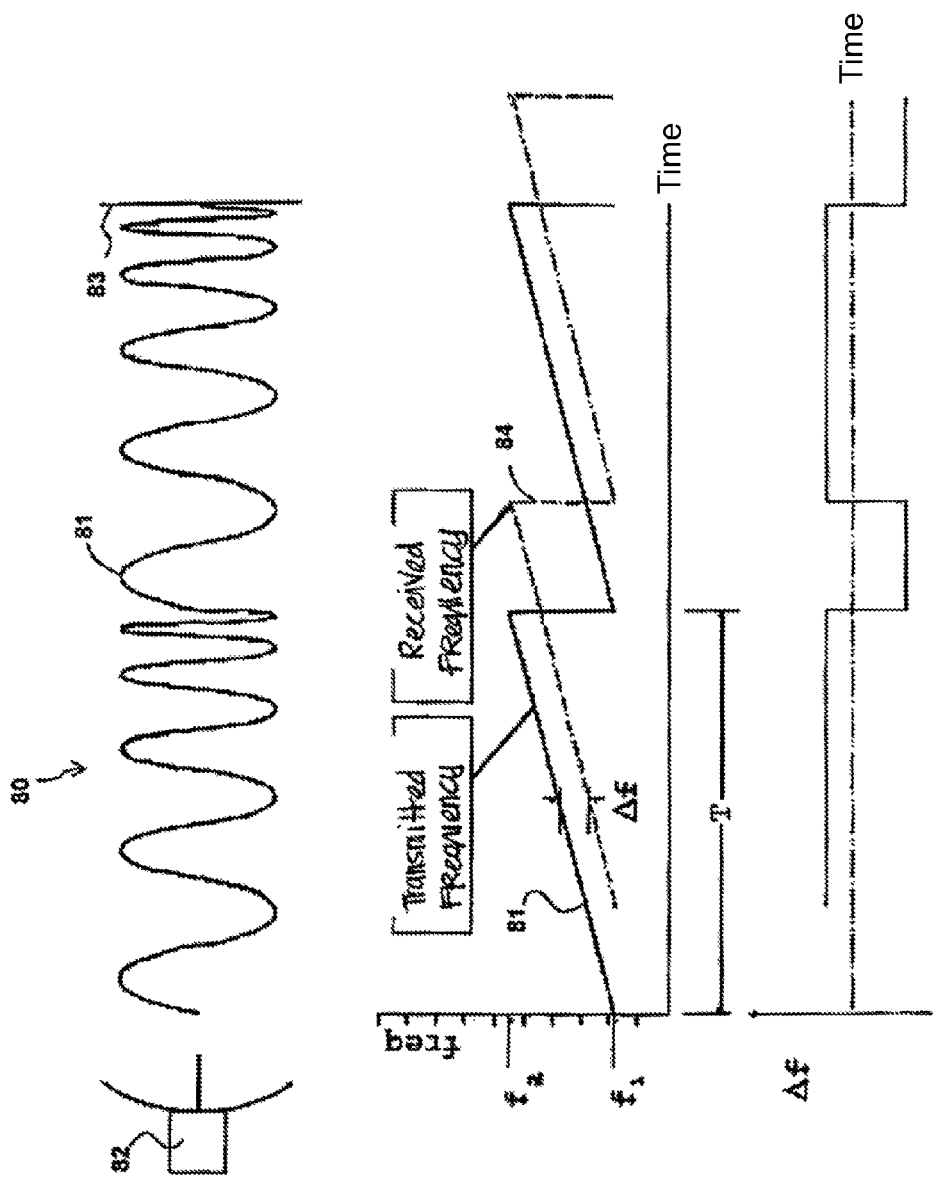
FIG. 9 is a schematic diagram which illustrates theory of operation for frequency modulated continuous wave (FMCW) RADAR.

Referring next to FIG. 9 of the drawings, a schematic diagram which illustrates theory of operation for frequency modulated continuous wave (FMCW) RADAR system 80 is illustrated. A transmitted frequency 81 is emitted from a transmitter 82. A received frequency 84 is returned from the target 83. The simplest way to modulate the wave is to linearly increase the frequency such that the transmitted frequency 81 will change at a constant rate $\Delta f$, as illustrated in FIG. 9.

Figure 10:
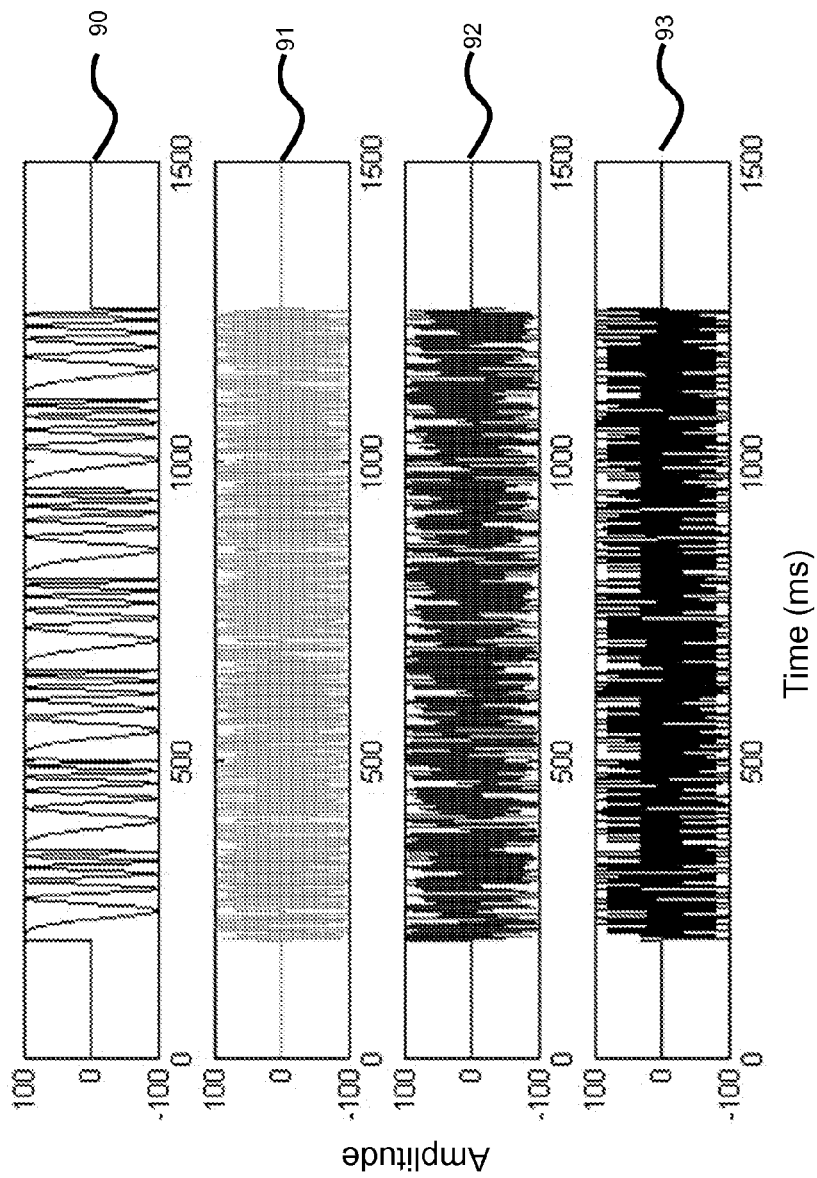
FIG. 10 is a graph which illustrates FMCW RADAR for each of the pulse waveforms illustrated in FIG. 1.

The FMCW RADAR system 80 measures the instantaneous difference between the transmitted frequency 81 and the received frequency 84, $\Delta f$. This difference is directly proportional to the time delay, $\Delta t$, which is takes the radar signal to reach the target 83 and return. From this the range can be found using the usual formula, $R = c\Delta t/2$. The time delay can be found as follows:

$$\Delta t = T\Delta f/(f_2 - f_1) \quad (14)$$

where:

$f_2$=maximum frequency
$f_1$=minimum frequency
T=period of sweep from $f_1$ to $f_2$,
and $\Delta f$=the difference between transmitted and received.
Combining these equations into a single form for the range $$R = 2cT\Delta f/(f_2-f_1) \tag{15}$$

where $\Delta f$ is the difference between the transmitted frequency 81 and the received frequency 84 (when both are from the same sweep, i.e. when it is positive). The linear FMCW pulse 90, the log FM FMCW pulse 91, the inverse FM FMCW pulse 92 and the random sinusoid FM FMCW pulse 93 are shown below in FIG. 10.

Figure 11:
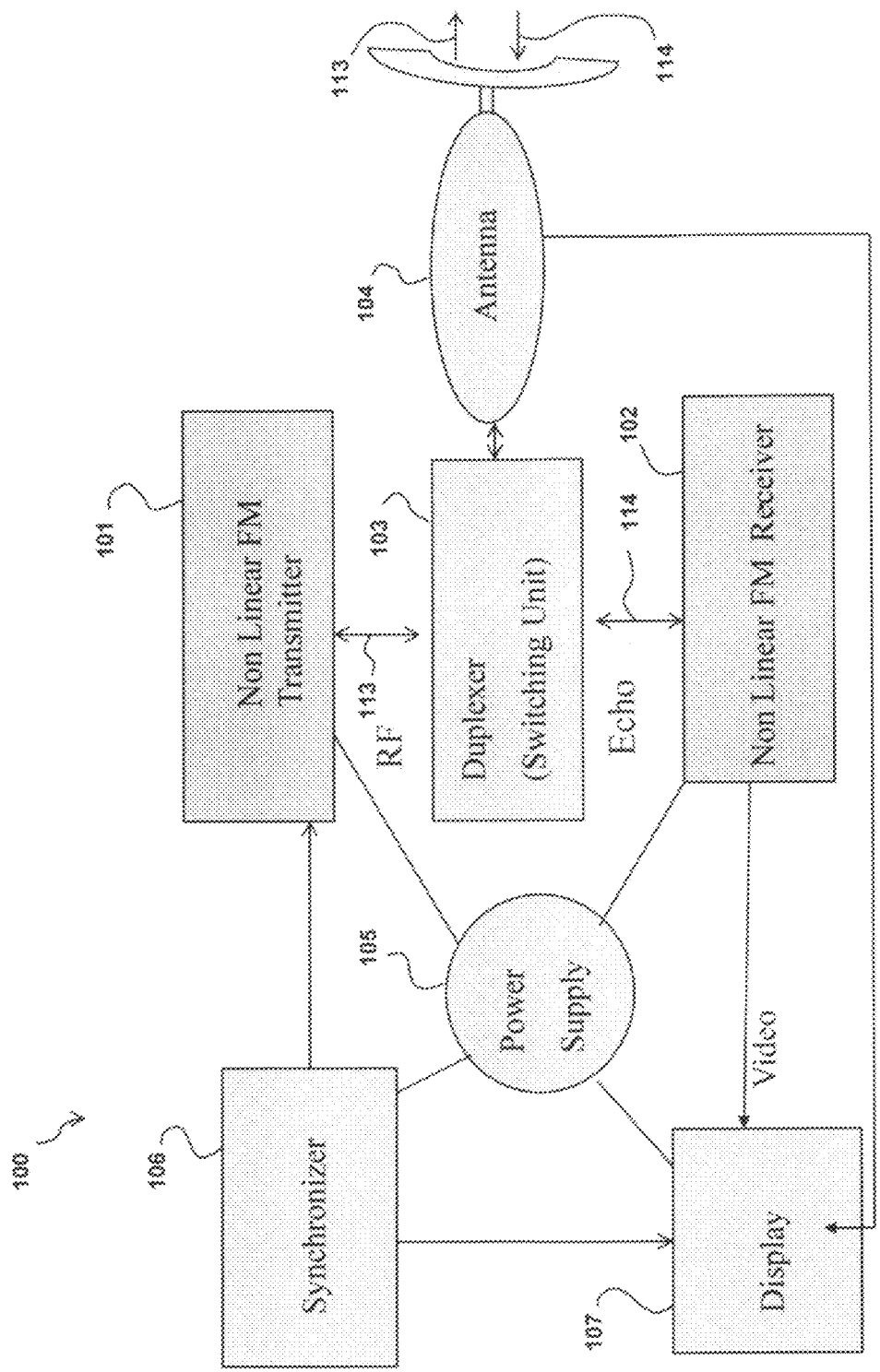
FIG. 11 is a block diagram of an illustrative embodiment of a non-linear FM pulse compression system.

Referring next to FIG. 11 of the drawings, a block diagram 100 of an illustrative embodiment of a non-linear FM pulse compression system, hereinafter system, is illustrated. The system 100 may include a non-linear FM transmitter 101 and a non-linear FM receiver 102. A duplexer or switching unit 103 may interface with the non-linear FM transmitter 101 and the non-linear FM receiver 102. An antenna 104 may interface with the duplexer 103. A synchronizer 106 may interface with the non-linear FM transmitter 101. A display 107 may interface with the non-linear FM receiver 102, the antenna 104 and the synchronizer 106. A power supply 105 may be connected to the non-linear FM transmitter 101, the non-linear FM receiver 102, the synchronizer 106 and the display 107.

In some embodiments, the non-linear FM transmitter 101 may be adapted to modulate the frequency of an input pulse signal by increasing the frequency of the input pulse signal as a logarithmic function of the frequency of the samples in the input pulse signal, as expressed by equation (3) herein above, to generate an output non-linear FM chirp signal 113. In some embodiments, the non-linear FM transmitter 101 may be adapted to modulate the frequency of an input pulse signal such that the frequency changes in the non-linear FM chirp signal 113 are inversely proportional to the frequency of the samples in the input pulse signal as expressed by equation (4) herein above. In some embodiments, the non-linear FM transmitter 101 may be adapted to modulate the frequency of the sinusoidal input pulse signal such that the non-linear FM chirp signal 113 is a random permutation of the output of the sinusoidal input pulse signal as expressed by equation (5a) herein above. In some embodiments, the non-linear FM transmitter 101 may be adapted to modulate the frequency of the input pulse signal such that the non-linear FM chirp signal 113 is a random permutation of the input to the sinusoidal input pulse signal as expressed by equation (5b) herein above.

The non-linear FM transmitter 101 may be adapted to emit the non-linear FM signal 113 to the duplexer 103. Through the duplexer 103, the antenna 104 may be adapted to emit the non-linear FM chirp signal 113 which is generated by the non-linear FM transmitter 101 to a target (not illustrated). The non-linear FM receiver 102 may be adapted to receive a return signal 114 from the target through the duplexer 103. The synchronizer 106 may ensure that the return signal 114 is reliably interpreted by the non-linear FM receiver 102. The non-linear FM receiver 102 may additionally be adapted to auto-correlate the return signal 114 with the non-linear FM chirp signal 113 which is emitted by the antenna 104. The display 107 may be adapted to receive the auto-correlated return signal from the non-linear FM receiver 102 and display the image of the target which is generated from the auto-correlated return signal.

Figure 13:
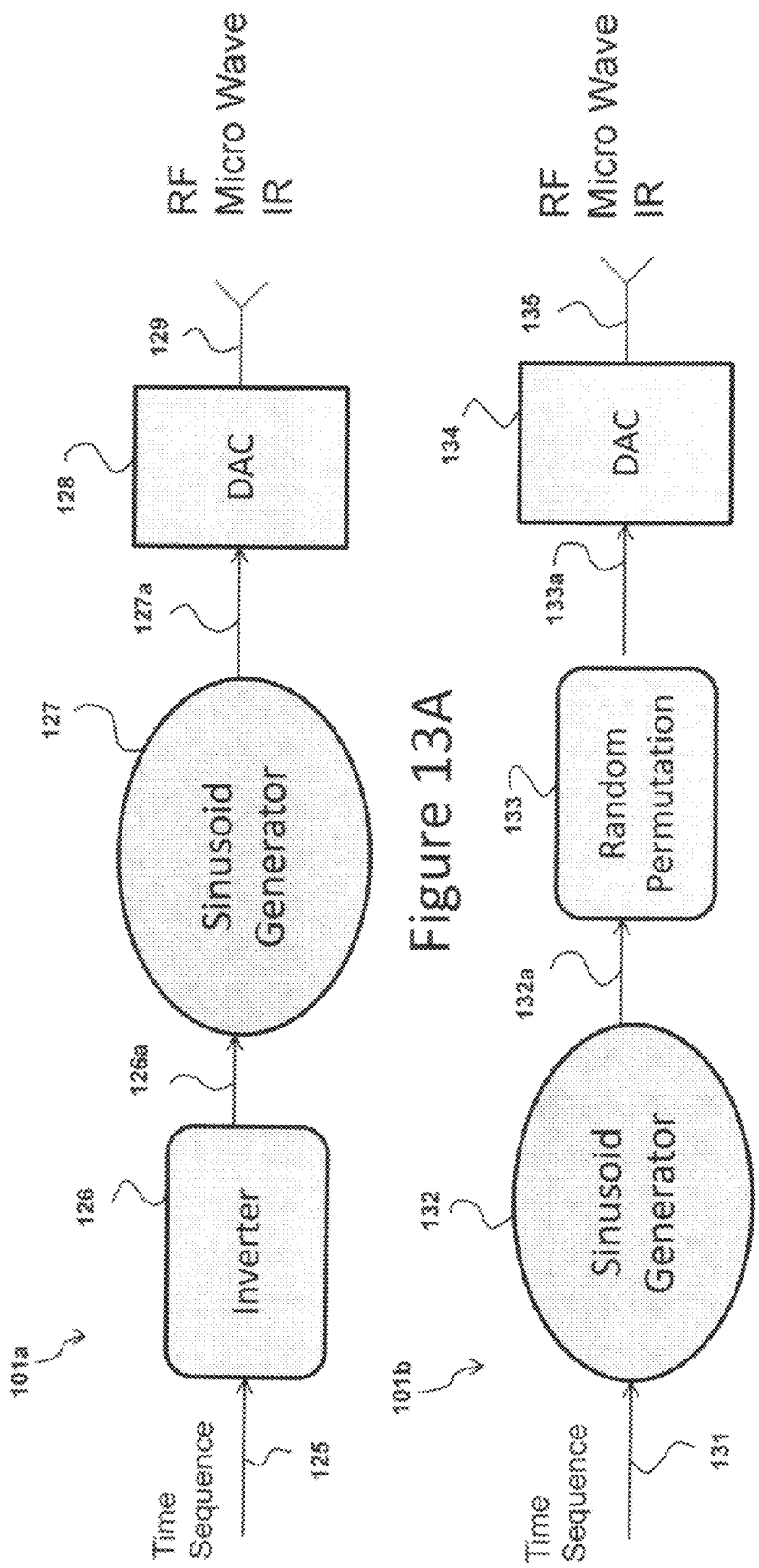
FIG. 13A is a block diagram of an inverse FM modulator pulse generator which is suitable for implementation of an illustrative embodiment of the non-linear FM pulse compression system.
FIG. 13B is a block diagram of a random sinusoid pulse generator which is suitable for implementation of an illustrative embodiment of the non-linear FM pulse compression system.

Referring next to FIG. 13A of the drawings, in some embodiments, the non-linear FM transmitter 101 may include an inverse FM modulator pulse generator 101a. The inverse FM modulator pulse generator 101a may be adapted to modulate the frequency changes in an input pulse signal such that the frequency changes in the output non-linear FM chirp signal are inversely proportional to the frequency of the samples in the input pulse signal as expressed by equation (4) herein above. The inverse FM modulator pulse generator 101a may include an inverter 126, a sinusoid generator 127 which interfaces with the inverter 126 and a digital to analog converter (DAC) 128 which interfaces with the sinusoid generator 127. An antenna 129 may interface with the DAC 128.

The inverter 126 may be adapted invert the time sequence 125 of an input pulse signal and emit an inverter output signal 126a having the inverted time sequence. The sinusoid generator 127 may be adapted to receive the inverter output signal 126a from the inverter 126 and generate a sinusoidal pulse 127a having the inverted time sequence. The digital to analog converter (DAC) 128 may be adapted to receive the sinusoidal pulse 127a from the sinusoid generator 127 and convert the sinusoidal pulse 127a from a digital signal to an analog non-linear FM chirp signal. The antenna 129 may be adapted to emit the non-linear FM chirp signal which is received from the DAC 128. Therefore, the frequency changes in the output non-linear FM chirp signal are inversely proportional to the frequency of the samples corresponding to the original time sequence 125 in the input sinusoidal pulse.

Referring next to FIG. 13B of the drawings, in some embodiments, the non-linear FM transmitter 101 may include a random sinusoid pulse generator 101b. The random sinusoid pulse generator 101b may be adapted to produce frequency changes of the non-linear FM chirp signal by a random permutation of the input pulse signal to generate a random sinusoidal non-linear FM chirp signal as expressed by equation (5a) herein above. The random sinusoid pulse generator 101b may include a sinusoid generator 132, a random permutation component 133 which interfaces with the sinusoid generator 132, a digital to analog converter (DAC) 134 which interfaces with the random permutation component 133 and an antenna 135 which interfaces with the DAC 134.

The sinusoid generator 132 may be adapted to generate a sinusoidal input pulse signal 132a having a time sequence 131. The random permutation component 133 may be adapted to produce a random permutation of the input sinusoidal pulse signal 132a and transmit a random sinusoidal pulse signal 133a to the DAC 134. The DAC 134 may be adapted to convert the digital random sinusoidal pulse signal 133a into an analog non-linear FM chirp signal which is emitted by the antenna 135.

Figure 12:
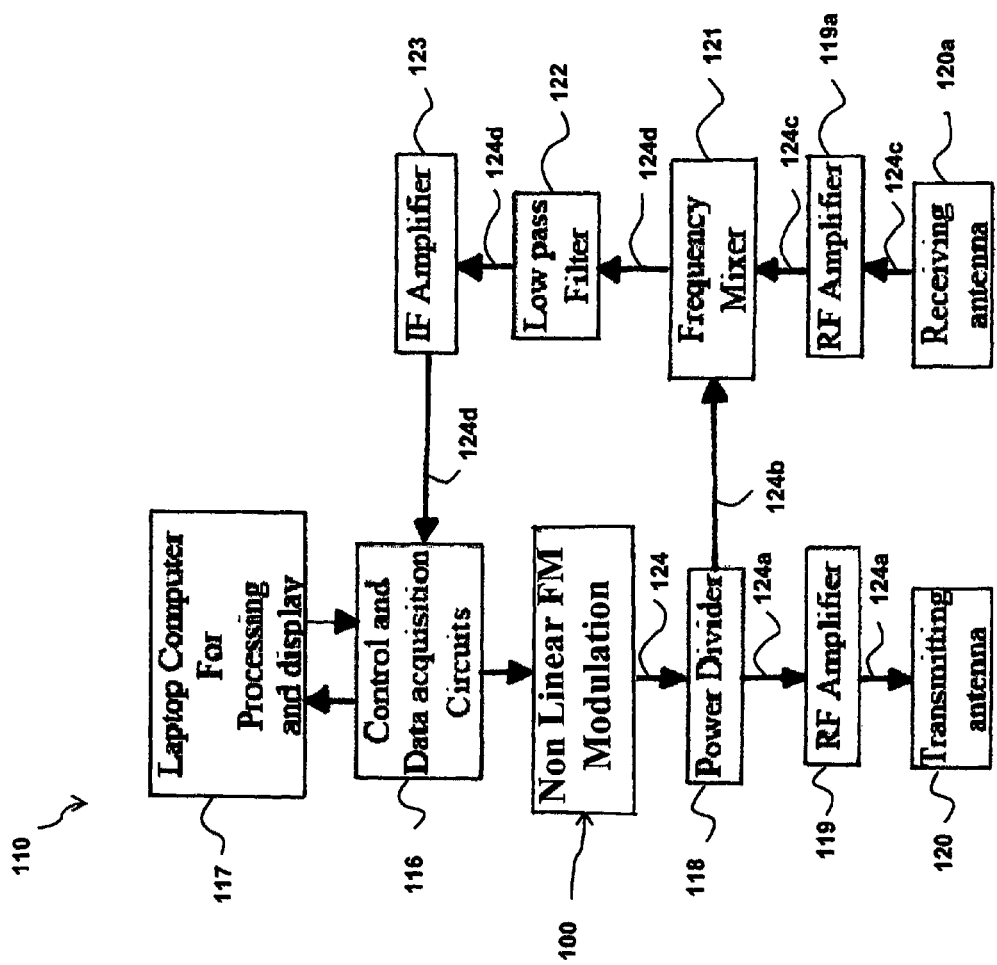
FIG. 12 is a block diagram of an illustrative embodiment of a non-linear FMCW laser.

Referring next to FIG. 12 of the drawings, a block diagram of an illustrative embodiment of a non-linear FM CW laser is generally indicated by reference numeral 110. The non-linear FM CW laser 110 may include a non-linear FM pulse compression system 100. Control and data acquisition circuits 116 may interface with the system 100. A laptop or other computer 117 may interface with the control and data acquisition circuits 116 for data processing and display purposes. A power divider 118 may also interface with the system 100. An RF amplifier 119 may interface with the power divider 118. A transmitting antenna 120 may interface with the RF amplifier 119.

The non-linear FM CW laser 110 may also include a receiving antenna 120a. An RF amplifier 119a may interface with the receiving antenna 120a. A frequency mixer 121 may interface with the RF amplifier 119a and with the power divider 118. A low pass filter 122 may interface with the frequency mixer 121. An IF amplifier 123 may interface with the low pass filter 122. The control and data acquisition circuits 116 may interface with the IF amplifier 123.

In operation of the non-linear FM CW laser 110, the oscillator of the system 100 emits a non-linear frequency-modulated sinusoidal wave signal 124. The power divider 118 divides the signal 124 into a transmitted signal 124a which is received by the RF amplifier 119 and a reference signal 124b which is received by the frequency mixer 121. After the RF amplifier 119 amplifies the transmitted signal 124a, the transmitting antenna 120 transmits the transmitted signal 124a to a target (not illustrated).

The receiving antenna 120a receives the reflected signal 124c from the target. The RF amplifier 119a amplifies the reflected signal 124c, and the frequency mixer 121 receives the amplified reflected signal 124c. At the frequency mixer 121, the reflected signal 124c mixes with the reference signal 124b. A mixed signal 124d, which is a modulated low frequency sinusoidal signal the main frequency of which is equal to the frequency difference between the reference signal 124b and the reflected signal 124c, is obtained from the output of the frequency mixer 121 and passes through the low pass filter 122 and the IF amplifier 123, respectively. At the control and data acquisition circuits 116, the mixed signal 124d is Fourier transformed into a frequency domain. The spectrum which appears on the laptop computer 117 displays all the reflection events and travel time delays between reflection events which can be calculated using the parameters such as the start and stop frequencies of the modulated oscillator of the system 100, the scanning time period and the frequency difference between reflection events.

Figure 14:
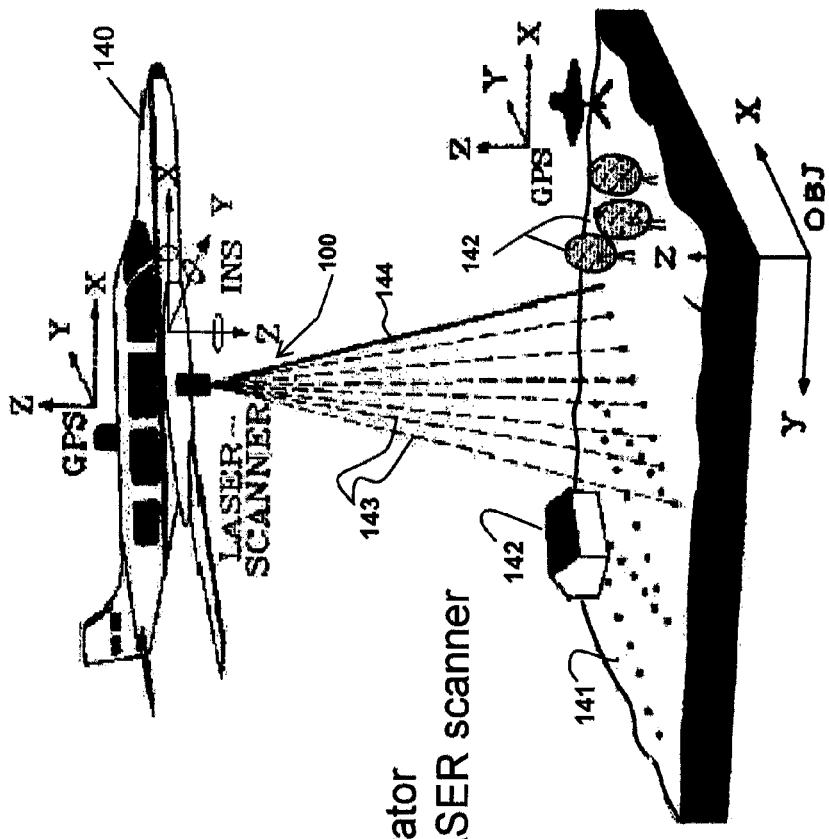
FIG. 14 is a schematic diagram which illustrates implementation of an illustrative embodiment of the non-linear FM pulse compression system in imaging targets on the ground from an aircraft.

Referring to FIG. 14 of the drawings, a schematic diagram which illustrates implementation of an illustrative embodiment of the non-linear FM pulse compression system 100 in imaging targets on the ground 141 from an aircraft 140 via LIDAR (Light Detection And Ranging) is illustrated. LIDAR is an optical remote sensing technology that measures properties of scattered light to find range and/or other information of a distant target. The prevalent method to determine distance to an object 142 or surface 141 is to use laser pulses 143. Like radar technology, which uses radio waves, the range to an object 142 is determined by measuring the time delay between transmission of a pulse 143 and detection of the reflected signal 144.

A recent addition to a police officer's speed detection arsenal is LIDAR (Laser Infrared Detection And Ranging). To measure a vehicle's speed, LIDAR determines how long it takes a light pulse to travel from the LIDAR gun to the vehicle and back. From this information, LIDAR can quickly find the distance between the gun and the vehicle. By making several measurements and comparing the distance the vehicle traveled between measurements, LIDAR very accurately determines the vehicle's speed. LIDAR uses a laser beam of invisible infrared light. The beam reflects off any flat surface on the vehicle. Since the beam is very narrow, it is impossible for any laser detector to determine the distance between the LIDAR source and the vehicle.

Just as there are two types of RADAR, there are also two types of lasers: Pulsed Lasers and Continuous Wave (CW) Lasers, which are used in LIDAR applications. The present disclosure includes use of the non-linear FM pulse compression system 100 for use in ranging and Doppler measurement applications.

Figure 15:
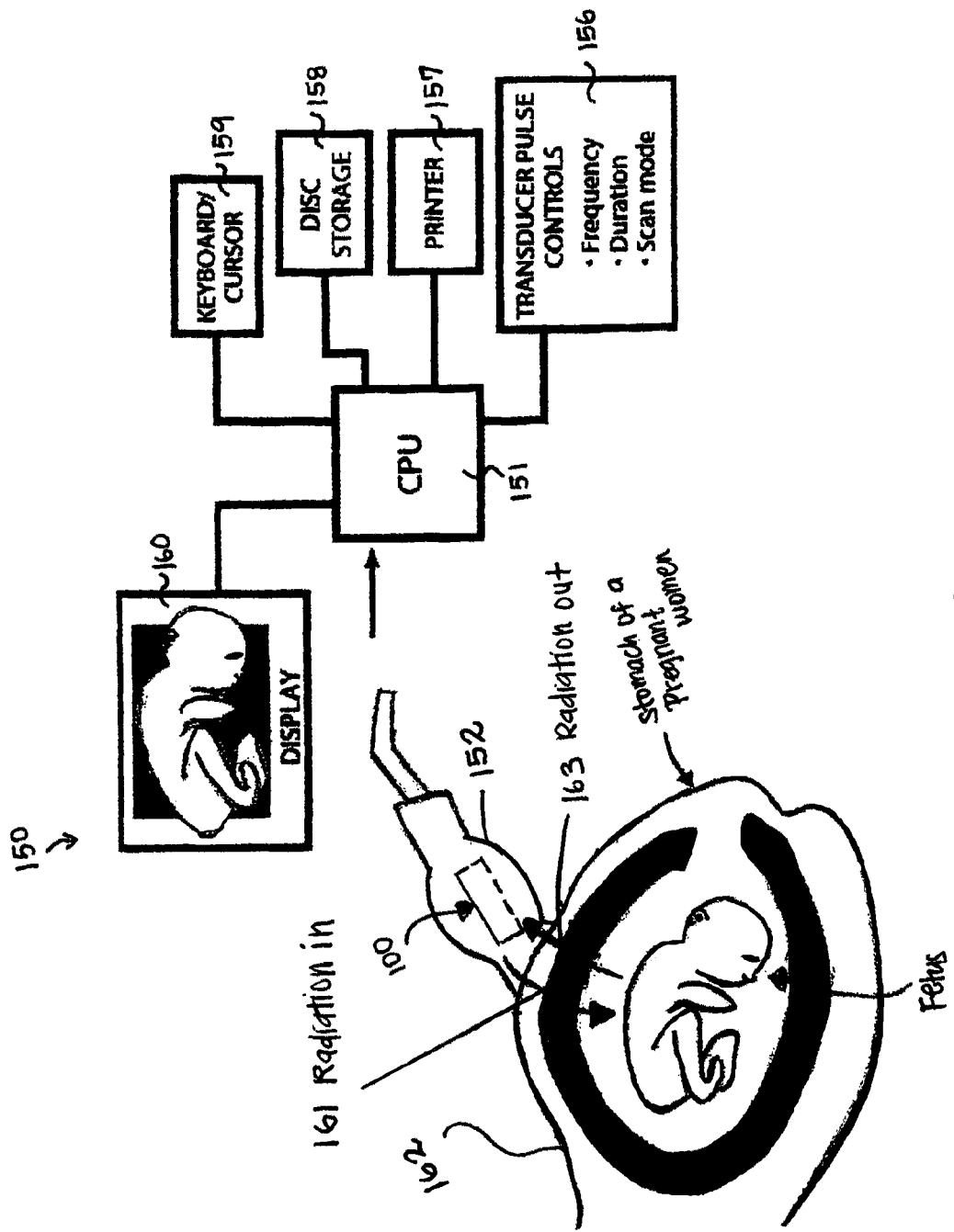
FIG. 15 is a schematic diagram which illustrates implementation of an illustrative embodiment of the non-linear FM pulse compression system in an ultrasonic imaging application.

Referring next to FIG. 15 of the drawings, a high-resolution medical ultrasound system 150 which utilizes an illustrative embodiment of the pulse compression system 100 is illustrated. The system 150 may include an ultrasound transducer 152 into which the pulse compression system 100 is installed. A CPU 151 may interface with the ultrasound transducer 152. External devices may interface with the CPU 151. The external devices may include transducer pulse controls 156, a printer 157, a disc storage device 158, a keyboard/cursor 159 and a display 160, for example and without limitation.

The pulse compression system 100 in the ultrasound transducer 152 transmits high frequency sound pulses 161 into a patient's body 162. The sound pulses 161 travel through the patient's body 162, passing through different types of tissue. Although the average speed of sound through human tissues is 1540 m/s, it does vary with exact tissue type. While the speed of sound through fat is 1459 m/s, it passes through bone at 4080 m/s. When sound encounters two adjacent tissue types with different acoustic properties, a proportion of the sound energy is reflected as reflected sound pulses 163. These boundaries between different tissue types are called acoustic interfaces.

The amount of reflected sound pulses 163 reflected back from an acoustic interface depends on a property of the materials on either side of the interface called acoustic impedance. The acoustic impedance of a material is simply the density of the material multiplied by the speed at which sound travels through the material.

Figure 16:
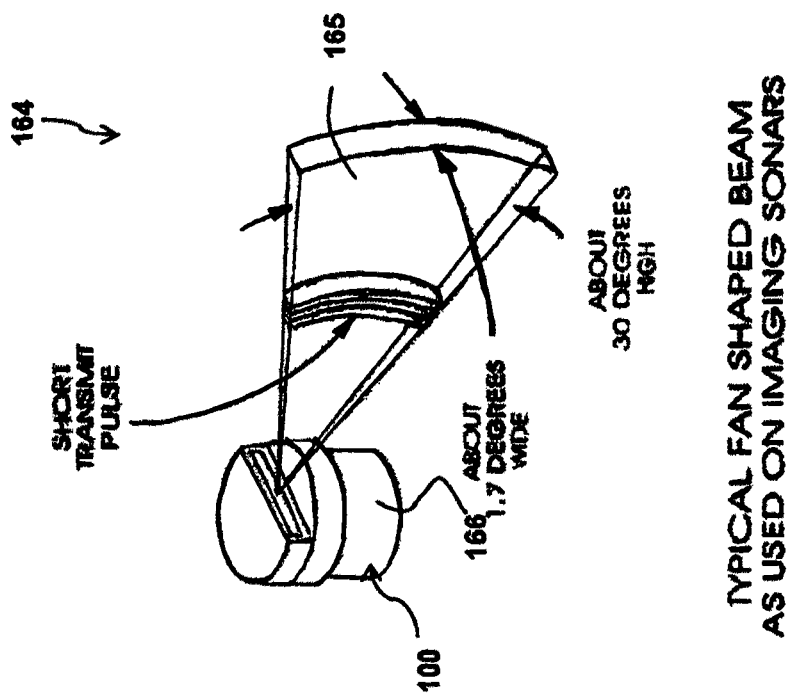
FIG. 16 is a schematic diagram which illustrates implementation of an illustrative embodiment of the non-linear FM pulse compression system in a high resolution sonar application.

Referring next to FIG. 16 of the drawings, a high resolution sonar system 164 which utilizes an illustrative embodiment of the pulse compression system 100 is illustrated. The pulse compression system 100 of the high resolution sonar system 164 can be used to power and drive the sonar beam generators 166 of the pulse compression system 100 to emit a sonar pulse 165 which may have a fan shape, as illustrated. The high resolution sonar system 164 uses sound propagation (usually underwater, as in submarine navigation) to navigate, communicate with or detect other vessels. There are two types of technology which share the name "sonar": passive sonar is essentially listening for the sound made by vessels; active sonar is emitting pulses of sounds and listening for echoes. Sonar may be used as a means of acoustic location and of measurement of the echo characteristics of "targets" in the water. Acoustic location in air was used before the introduction of radar.

Referring next to FIG. 17 of the drawings, a high resolution synthetic radar system 170 which utilizes an illustrative embodiment of the pulse compression system 100 is illustrated. The pulse compression system 100 may be provided in a spacecraft 171 and emits a high resolution synthetic radar pulse 175 against a target 174. A reflected signal (not illustrated) is reflected from the target 174 back to the pulse compression system 100. A data processor 172 interfaces with the system 100 and auto-correlates the reflected signal and the emitted high resolution synthetic radar pulse 175. A high resolution image of the target 174 is shown on a display 173 which interfaces with the data processor 172.

Beginning with the launch of SESAT in 1978, Synthetic Aperture Radar (SAR) have provided a wealth of information on such diverse phenomena as surface waves, internal waves, currents, upwelling, shoals, sea ice, wind and rainfall. SAR is the premier sensor for such phenomena because it is sensitive to small surface roughness changes of the order of Radar wavelength (1 millimeter down to several centimeters). It is also independent of solar illumination and is generally unaffected by cloud cover. Most modern RADARs (including SARs) transmit a pulse 175 known as linear modulated waveform and use the standard RADAR principles of range resolution and Doppler shift. Hence the linear FM pulse generator can be replaced with the pulse compression system 100 to produce higher solution in SAR images on the display 173.

Figure 18A:
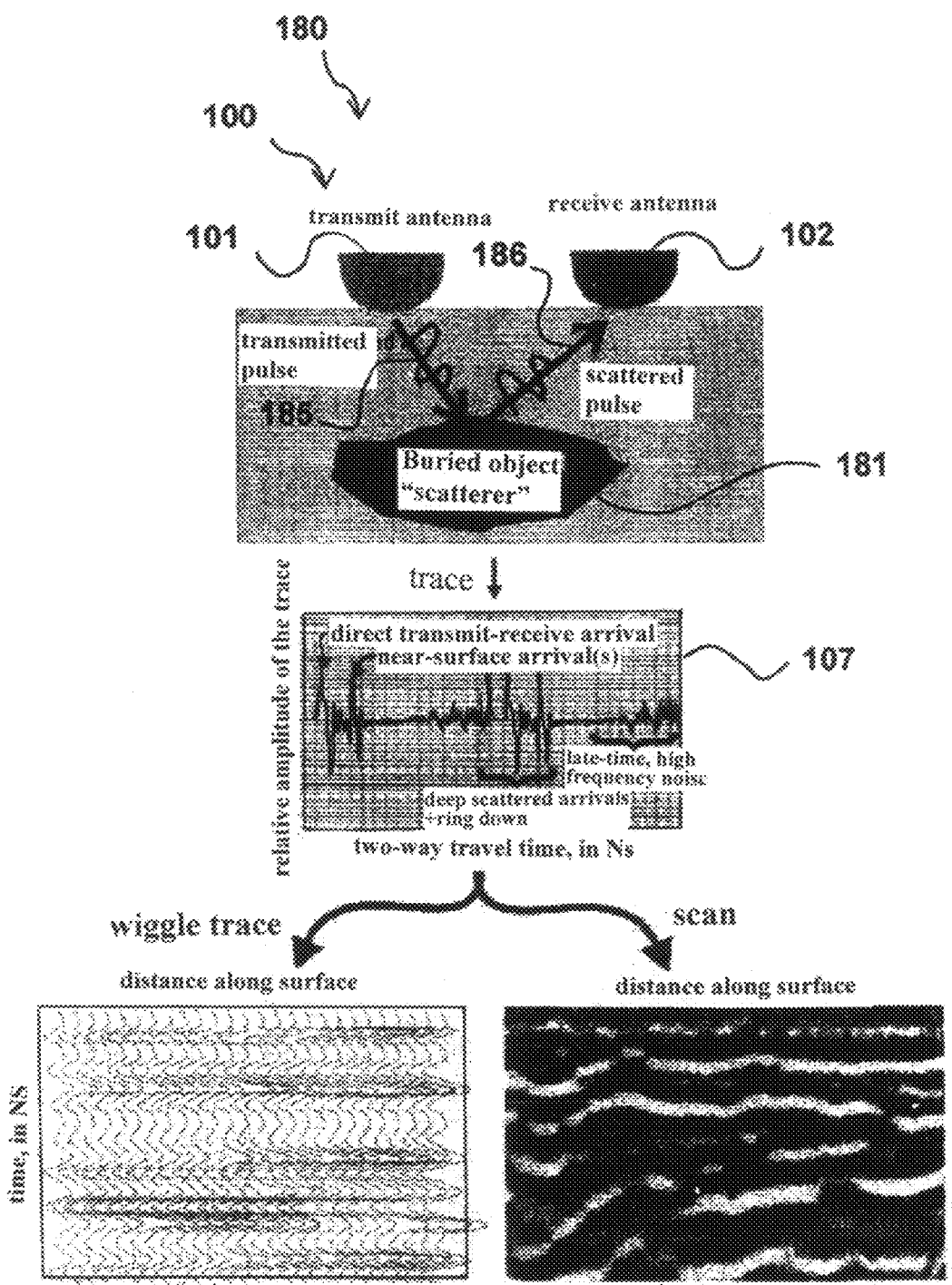
FIGS. 18A-18C are schematic diagrams which illustrate implementation of an illustrative embodiment of the non-linear FM pulse compression system in a high resolution ground penetrating radar application.
Figure 18B:
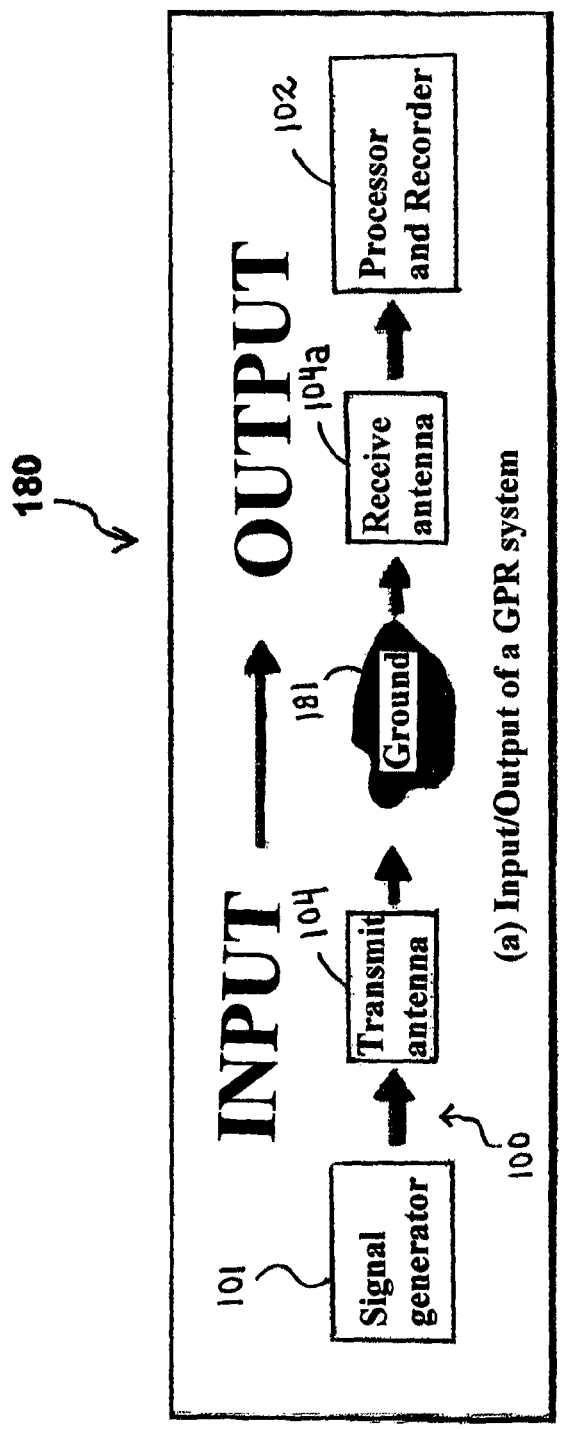
Figure 18C:
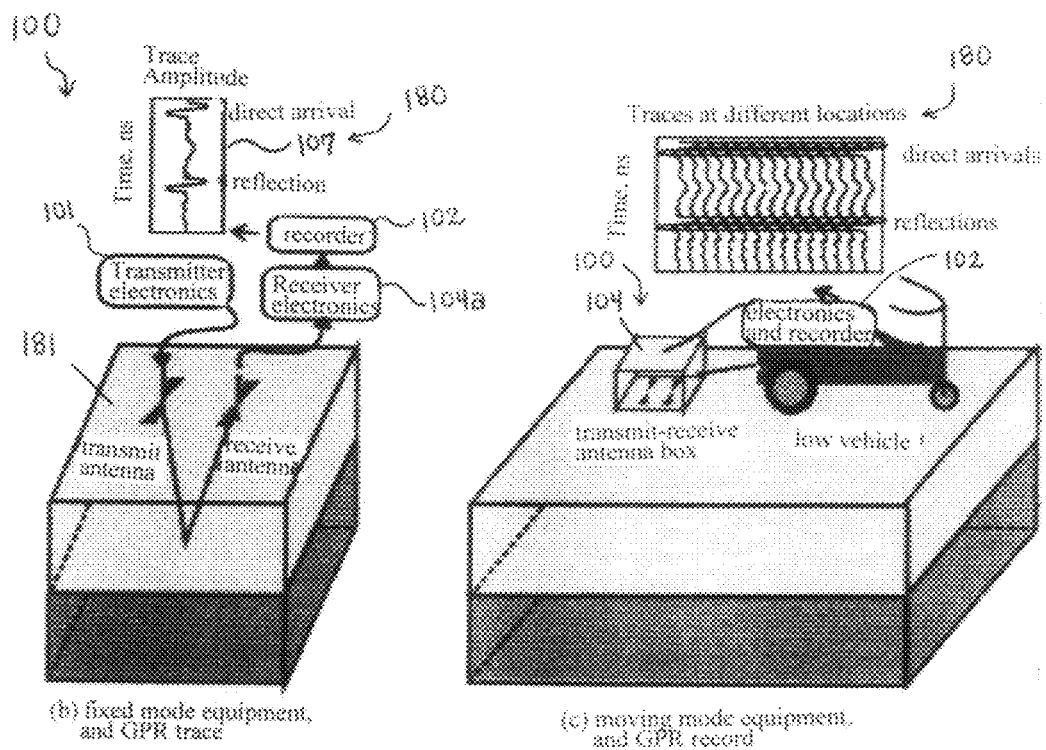

Referring next to FIGS. 18A-18C of the drawings, a high resolution ground penetrating radar system 180 which utilizes an illustrative embodiment of the pulse compression system 100 is illustrated. Ground Penetrating RADAR (GPR) utilizes a very short burst of radio-frequency energy as a pulse 185 which is transmitted from the non-linear FM transmitter 101 via the transmit antenna 104 (FIG. 18B) of the pulse compression system 100 and radiated into the ground 181 to detect discontinuities in the ground 181. The scattered pulse 186 is reflected from the ground 181 and detected by a receive antenna 104a. A signal processor and recorder 102 auto-correlates the scattered pulse 186 and the transmitted pulse 185 and records or displays a high-resolution image of the ground 181 or objects or discontinuities in the ground 181 on a display 107, as illustrated in FIGS. 18A and 18B. Alternative applications of the pulse compression system 100 in implementation of the high resolution ground penetrating radar system 180 are illustrated in FIG. 18C.

The objects or discontinuities in the ground 181 can be cavities, voids, transitions between soil and rock, filled areas and/or buried objects. The performance of conventional GPRs is limited by attenuation of the transmitted pulse in moist soils, especially soils having high clay content. GPRs are used to detect a boundary between rock and air (a cave or cavity) or between one type of soil and another (for example undisturbed soil-to back-filled soil). The strength of the echo signal is dependent on the absorption of the signal to and from the radar to the target, the size and shape of the target, and the degree of discontinuity at the reflecting boundary.

Referring next to FIG. 19 of the drawings, a high resolution air traffic control system 190 which utilizes an illustrative embodiment of the pulse compression system 100 is illustrated. The air traffic control system 190 may include a ground control 191 having a ground control tower 192. The pulse compression system 100 may be provided in the ground control tower 192. An antenna 104 of the pulse compression system 100 emits pulses 193 which are reflected from flying aircraft 194. Return pulses (not illustrated) reflected from the aircraft 194 are received by the antenna 104 and processed as was heretofore described with respect to FIG. 11 to generate a high-resolution image of the aircraft 194.

Air traffic control systems are critically dependent on the use of RADAR technology for the safety of tens of thousands of aircrafts and millions of passengers every day. With the increase in air traffic, there is need for high resolution air traffic tracking systems. Currently, pulsed radars and FMCW radars are used for range measurement and Doppler measurements. With the use of the non-linear FM pulse compression system 100, the performance of the air traffic systems 190 can be significantly improved with more accurate estimation and detection of aircraft 194. In particular, the relative positions of those aircraft 194 which would otherwise come within dangerously close proximity to each other may be detected sufficiently early to prevent such close proximity and avert potential aviation accidents.

A free electron laser (FEL) is a laser which shares the same optical properties as conventional lasers such as emission of an electron beam having coherent electromagnetic radiation which can reach high power but which uses some very different operating principles to form the beam. Unlike gas, liquid or solid-state lasers such as diode lasers, in which electrons are excited in bound atomic or molecular states, FELs use a relativistic electron beam as the lasing medium which moves freely through a magnetic structure (hence the term free electron). The free electron laser has the widest frequency range of any laser type and can be widely tunable, currently ranging in the wavelength from microwaves through terahertz radiation and infrared, to the visible spectrum, to ultraviolet, to X-ray.

Figure 20:
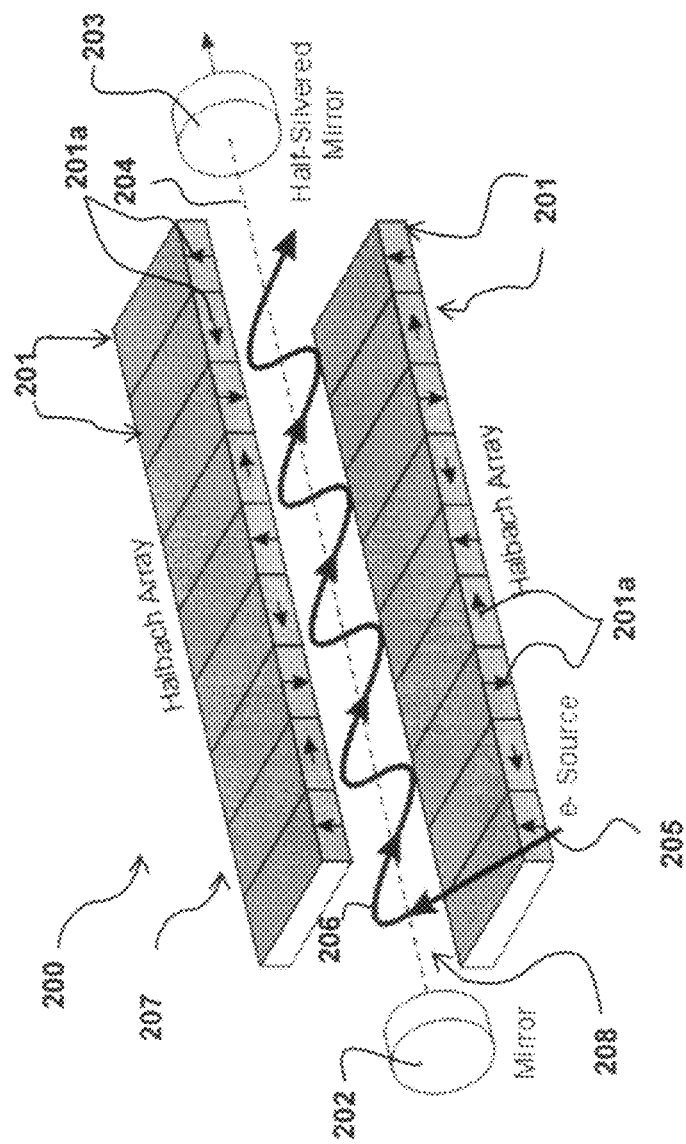
FIG. 20 is a schematic diagram which illustrates implementation of an illustrative embodiment of a free electron laser system.

Referring next to FIG. 20 of the drawings, a free electron laser system 200 is illustrated. In the free electron laser system 200, an FEL oscillator in the form of a "wiggler" or undulator 207 includes two parallel series of permanent magnets 201 having alternating poles 201a. A full-silvered mirror 202 and a half-silvered mirror 203 may be placed at opposite ends of the undulator 207. An electron source 205 is adapted to emit an electron beam 206 to almost light speed (relativistic speed) into a laser cavity 208 between the parallel series of magnets 201 and within a path of light 204 between the full-silvered mirror 202 and the half-silvered mirror 203. The array of magnets 201 of the undulator 207 forces the electrons in the electron beam 206 to follow a sinusoidal path. The acceleration of the electrons along the sinusoidal path of the electron beam 206 results in a release of a photon (synchroton radiation). Since the electron motion is in phase with the field of the light 204 already emitted, the fields add together coherently. Whereas conventional undulators would cause the electrons to radiate independently, instabilities in the undulators and the radiation they emit leads to bunching of the electrons, which continue to radiate in phase with each other.

Figure 21:
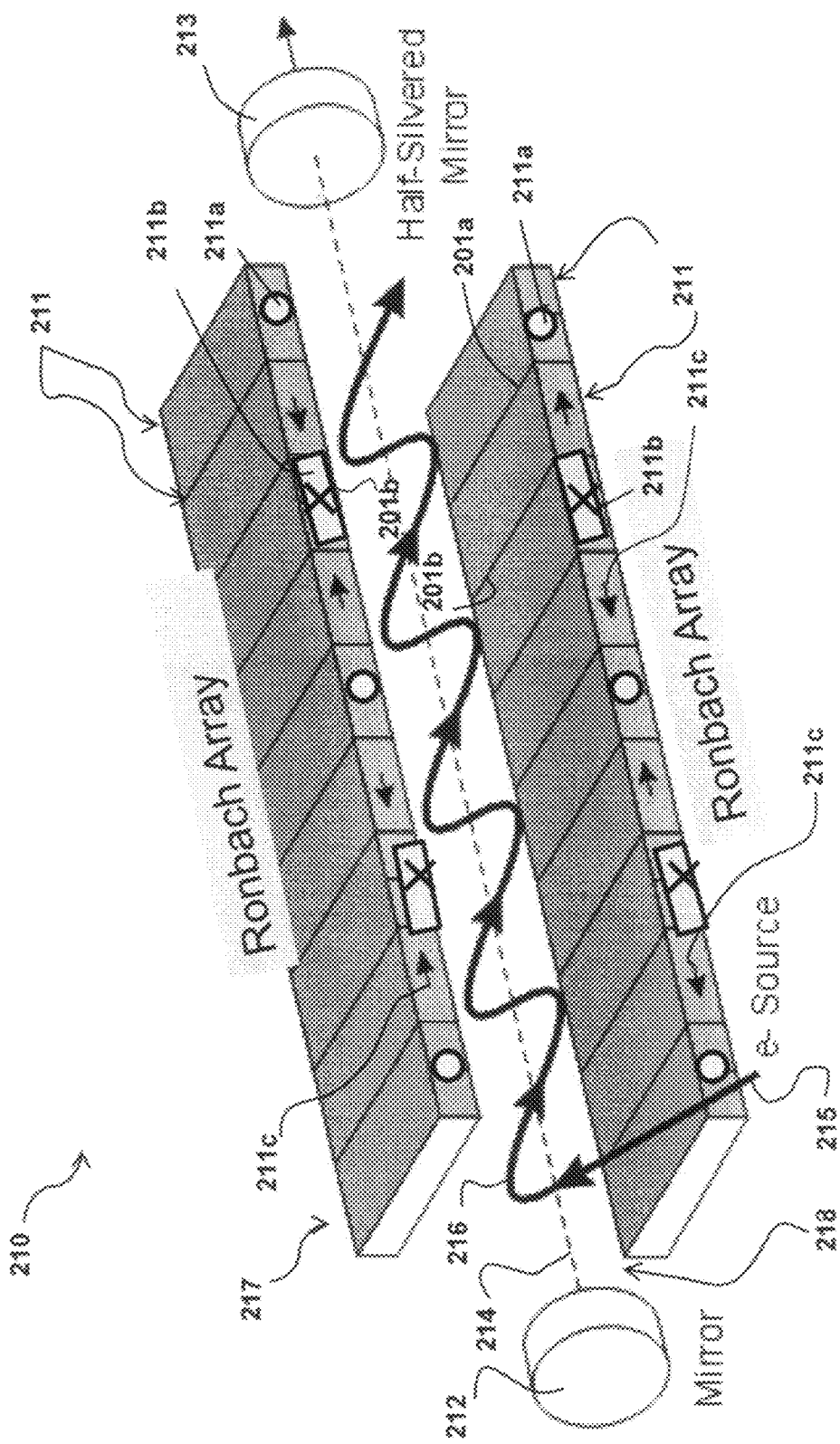
FIG. 21 is a schematic diagram which illustrates implementation of an alternative illustrative embodiment of a free electron laser system.

Referring next to FIG. 21 of the drawings, a schematic diagram which illustrates implementation of an alternative illustrative embodiment of a free electron laser system 210 is illustrated. In the free electron laser 210, each undulator 217 includes two parallel series of permanent magnets 211 each of which is a modified Halbach array (hereinafter referred to as a "Ronbach" array) in which the magnetic north pole 211a and the magnetic south pole 211b of alternating magnets face the same direction. A full-silvered mirror 212 and a half-silvered mirror 213 may be placed at opposite ends of the undulator 217. An electron source 215 is adapted to emit an electron beam 216 to almost light speed (relativistic speed) into a laser cavity 218 between the parallel series of magnets 201 and within a path of light 214 between the full-silvered mirror 212 and the half-silvered mirror 213. The Ronbach magnetic array of the undulator 217 may result in 71% increase of magnetic field as opposed to 41% increase of magnetic field for Halbach magnetic arrays.

Figure 22:
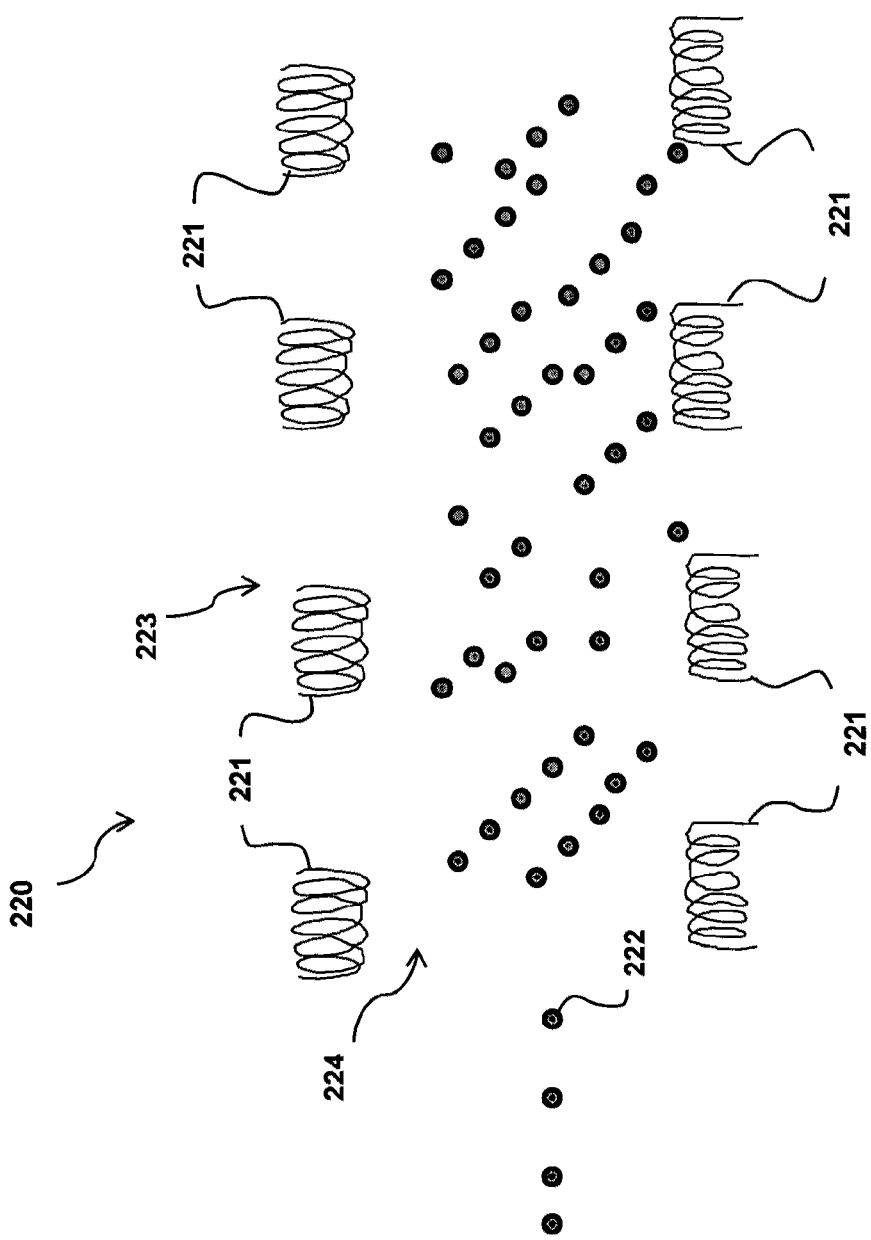
FIG. 22 is a schematic diagram which illustrates implementation of another alternative illustrative embodiment of a free electron laser system.

Referring next to FIG. 22 of the drawings, a schematic diagram which illustrates implementation of another alternative illustrative embodiment of a free electron laser system 220 is illustrated. The undulator 223 of the free electron laser system 220 may include two parallel series of electromagnets with random phase distribution 221. A laser cavity 220 may be defined between the parallel series of electromagnets with random phase distribution 221. Accordingly, the magnetic polarity of the electromagnets with random phase distribution 221 is changed at random, inducing a random modulation of the electron beam 222 as it is emitted through the laser cavity 220.

Figure 23:
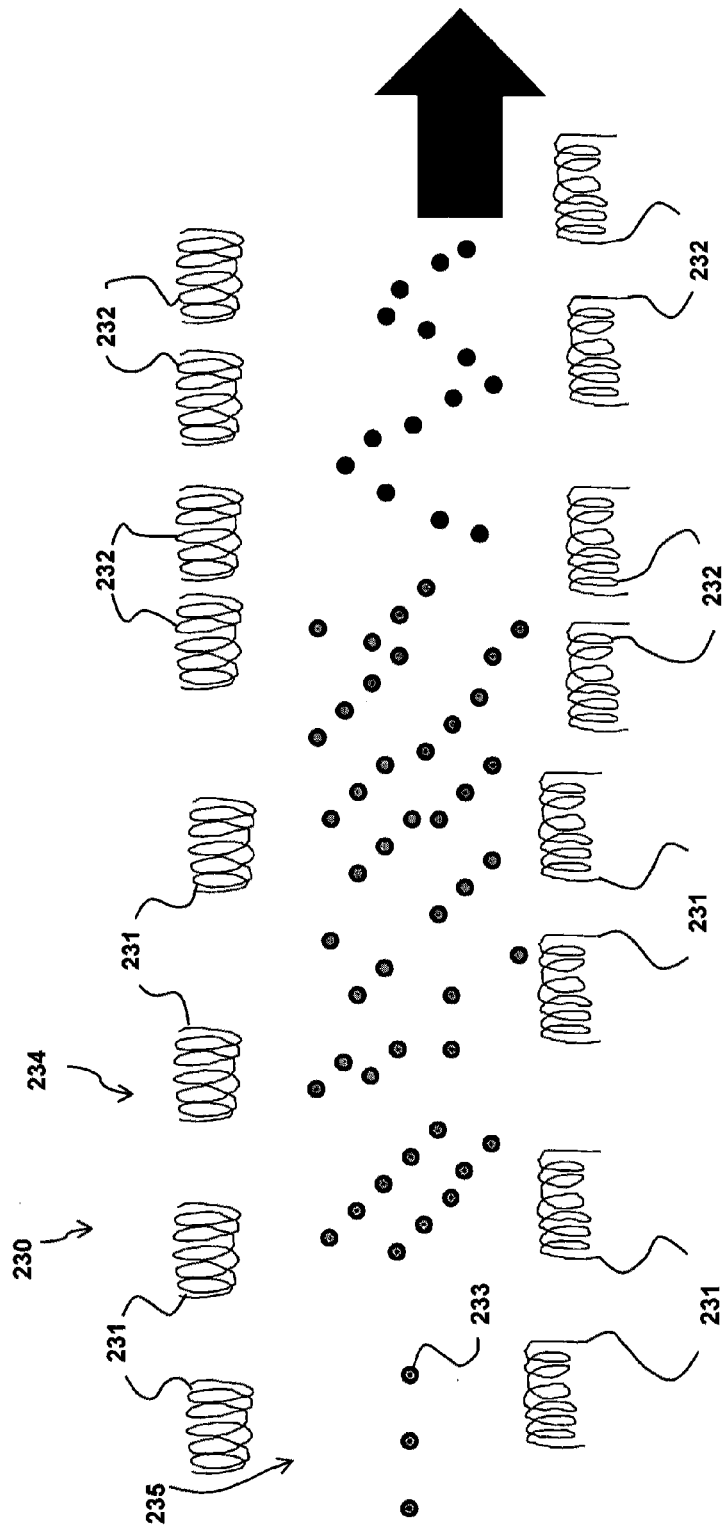
FIG. 23 is a schematic diagram which illustrates implementation of an illustrative embodiment of a free electron laser system.

Referring next to FIG. 23 of the drawings, a schematic diagram which illustrates implementation of an illustrative embodiment of a free electron laser system 230 is illustrated. The undulator 234 of the free electron laser system 230 may include two parallel series of electromagnets with random phase distribution 231 and electromagnets with alternating north and south poles 232. A laser cavity 235 may be defined between the parallel series of electromagnets with random phase distribution 221. Accordingly, the free electron laser system 230 may be operated in a two-cycle operation in which the electromagnets with random phase distribution 221 are energized during the first cycle and the electromagnets with alternating north and south poles 232 are energized during the second cycle. This causes the electron beam 233 to undergo several oscillations, resulting in radiation of intense concentrated energy in narrow energy bands of the spectrum as it is emitted through the laser cavity 235.

While the preferred embodiments of the disclosure have been described above, it will be recognized and understood that various modifications can be made in the disclosure and the appended claims are intended to cover all such modifications which may fall within the spirit and scope of the disclosure.

What is claimed is:

1. A non-linear frequency modulation (FM) pulse compression system, comprising:
    a non-linear FM transmitter configured to receive an input signal and transmit an output signal,
    wherein the non-linear FM transmitter is configured to modulate the frequency of the output signal according to a random permutation of samples of the input signal;
    at least one antenna interfacing with the non-linear FM transmitter; and
    a non-linear FM receiver interfacing with the at least one antenna,
    wherein the non-linear FM receiver is configured to auto-correlate the output signal with a return signal.

2. The system of claim 1 further comprising a display interfacing with the non-linear FM receiver and the antenna.

3. The system of claim 2 further comprising a synchronizer interfacing with the nonlinear FM transmitter and the display.

4. The system of claim 1 wherein the non-linear FM transmitter comprises a sinusoid generator, a random permutation component interfacing with the sinusoid generator and a digital-to-analog converter interfacing with the sinusoid generator.

5. A non-linear frequency modulation pulse compression method, comprising:
    providing an input signal;
    forming an output signal by modulating the frequency of the output signal according to a random permutation of samples of the input signal;
    transmitting the output signal against a target;
    receiving a return signal from the target; and
    auto-correlating the output signal with the return signal.

6. The method of claim 5 wherein forming an output signal comprises forming radar pulses and transmitting the output signal against a target comprises transmitting the radar pulses from an aircraft against ground targets.

7. The method of claim 5 wherein forming an output signal comprises forming sound pulses and transmitting the output signal against a target comprises transmitting the sound pulses from an ultrasound transducer against a human body.

8. The method of claim 5 wherein forming an output signal comprises forming sonar pulses.

9. The method of claim 5 wherein forming an output signal comprises forming high-resolution synthetic radar pulses.

10. The method of claim 5 wherein transmitting the output signal against a target comprises transmitting the output signal against a buried object.

11. The method of claim 5 wherein transmitting the output signal against a target comprises transmitting pulses against flying aircraft.

* * * * *